United States Patent
Hood et al.

(10) Patent No.: US 10,016,406 B2
(45) Date of Patent: Jul. 10, 2018

(54) INDAZOLE INHIBITORS OF THE WNT SIGNAL PATHWAY AND THERAPEUTIC USES THEREOF

(71) Applicant: Samumed, LLC, San Diego, CA (US)

(72) Inventors: John Hood, San Diego, CA (US); David Mark Wallace, San Diego, CA (US); Sunil Kumar KC, San Diego, CA (US)

(73) Assignee: Samumed, LLC, San Diego, CA (US)

( * ) Notice: Subject to any disclaimer, the term of this patent is extended or adjusted under 35 U.S.C. 154(b) by 0 days.

(21) Appl. No.: 15/681,035

(22) Filed: Aug. 18, 2017

(65) Prior Publication Data

US 2018/0153873 A1    Jun. 7, 2018

Related U.S. Application Data

(63) Continuation of application No. 15/184,553, filed on Jun. 16, 2016, now Pat. No. 9,763,927, which is a continuation of application No. 14/741,645, filed on Jun. 17, 2015, now Pat. No. 9,381,192, which is a continuation of application No. 14/334,005, filed on Jul. 17, 2014, now Pat. No. 9,090,613, which is a continuation of application No. 13/552,188, filed on Jul. 18, 2012, now Pat. No. 8,822,478, which is a continuation of application No. 12/852,706, filed on Aug. 9, 2010, now Pat. No. 8,252,812.

(60) Provisional application No. 61/232,603, filed on Aug. 10, 2009, provisional application No. 61/305,459, filed on Feb. 17, 2010.

(51) Int. Cl.

| | |
|---|---|
| *A61K 31/437* | (2006.01) |
| *A61K 31/4545* | (2006.01) |
| *A61K 31/541* | (2006.01) |
| *A61K 31/4178* | (2006.01) |
| *A61K 31/5377* | (2006.01) |
| *C07D 403/14* | (2006.01) |
| *C07D 403/04* | (2006.01) |
| *C07D 405/12* | (2006.01) |
| *A61K 31/454* | (2006.01) |
| *A61K 31/416* | (2006.01) |
| *C07D 231/56* | (2006.01) |
| *A61K 31/496* | (2006.01) |
| *A61K 31/4184* | (2006.01) |
| *C07D 471/04* | (2006.01) |
| *A61K 31/444* | (2006.01) |
| *A61K 31/4439* | (2006.01) |
| *C07D 409/12* | (2006.01) |
| *C07D 401/14* | (2006.01) |
| *C07D 487/08* | (2006.01) |
| *C07D 487/04* | (2006.01) |
| *C07D 403/12* | (2006.01) |
| *C07D 401/12* | (2006.01) |
| *A61K 31/551* | (2006.01) |
| *A61K 31/44* | (2006.01) |

(52) U.S. Cl.
CPC ........ *A61K 31/4545* (2013.01); *A61K 31/416* (2013.01); *A61K 31/4178* (2013.01); *A61K 31/4184* (2013.01); *A61K 31/437* (2013.01); *A61K 31/44* (2013.01); *A61K 31/444* (2013.01); *A61K 31/4439* (2013.01); *A61K 31/454* (2013.01); *A61K 31/496* (2013.01); *A61K 31/5377* (2013.01); *A61K 31/541* (2013.01); *A61K 31/551* (2013.01); *C07D 231/56* (2013.01); *C07D 401/12* (2013.01); *C07D 401/14* (2013.01); *C07D 403/04* (2013.01); *C07D 403/12* (2013.01); *C07D 403/14* (2013.01); *C07D 405/12* (2013.01); *C07D 409/12* (2013.01); *C07D 471/04* (2013.01); *C07D 487/04* (2013.01); *C07D 487/08* (2013.01)

(58) Field of Classification Search
CPC .................................................... A61K 31/437
USPC ......................................... 514/303, 256, 275
See application file for complete search history.

(56) References Cited

U.S. PATENT DOCUMENTS

| | | | |
|---|---|---|---|
| 4,164,559 | A | 8/1979 | Miyata et al. |
| 4,474,752 | A | 10/1984 | Haslam et al. |
| 5,922,733 | A | 7/1999 | Forbes et al. |
| 6,120,484 | A | 9/2000 | Silverstein |

(Continued)

FOREIGN PATENT DOCUMENTS

| | | |
|---|---|---|
| CN | 1394205 | 1/2003 |
| CN | 1671710 | 9/2005 |

(Continued)

OTHER PUBLICATIONS

"Application of Hamish Christopher Swan Wood, Norman Whittaker, Irene Stirling and Kyuji Ohta.," 582 F.2d 638 (Fed. Cir. 1978), 2 pages.

(Continued)

*Primary Examiner* — Niloofar Rahmani
(74) *Attorney, Agent, or Firm* — Fish & Richardson P.C.

(57) ABSTRACT

Indazole compounds for treating various diseases and pathologies are disclosed. More particularly, the present invention concerns the use of an indazole compound or analogs thereof, in the treatment of disorders characterized by the activation of Wnt pathway signaling (e.g., cancer, abnormal cellular proliferation, angiogenesis, Alzheimer's disease and osteoarthritis), the modulation of cellular events mediated by Wnt pathway signaling, as well as genetic diseases due to mutations in Wnt signaling components. Also provided are methods for treating Wnt-related disease states.

20 Claims, No Drawings

(56) References Cited

U.S. PATENT DOCUMENTS

| | | |
|---|---|---|
| 6,358,978 B1 | 3/2002 | Ritzeler et al. |
| 6,377,849 B1 | 4/2002 | Lenarz et al. |
| 6,440,102 B1 | 8/2002 | Arenberg et al. |
| 6,555,539 B2 | 4/2003 | Reich et al. |
| 6,648,873 B2 | 11/2003 | Arenberg et al. |
| 6,831,175 B2 | 12/2004 | Li et al. |
| 6,884,890 B2 | 4/2005 | Kania et al. |
| 6,897,208 B2 | 5/2005 | Edwards et al. |
| 6,911,211 B2 | 6/2005 | Eini et al. |
| 6,919,461 B2 | 7/2005 | Reich et al. |
| 7,008,953 B2 | 3/2006 | Kephart et al. |
| 7,064,215 B2 | 6/2006 | Renhowe et al. |
| 7,232,912 B2 | 6/2007 | Reich et al. |
| 7,285,565 B2 | 10/2007 | Zhu et al. |
| 7,429,609 B2 | 9/2008 | Ohi et al. |
| 7,452,993 B2 | 11/2008 | Arnold et al. |
| 7,468,376 B2 | 12/2008 | Rosales et al. |
| 7,482,342 B2 | 1/2009 | D'Orchymont et al. |
| 7,488,737 B2 | 2/2009 | Xie et al. |
| 7,491,710 B2 | 2/2009 | Cherrier et al. |
| 7,541,367 B2 | 6/2009 | Chiu et al. |
| 7,626,021 B2 | 12/2009 | Arnold et al. |
| 7,642,278 B2 | 1/2010 | Jansen et al. |
| 7,666,867 B2 | 2/2010 | Makriyannis et al. |
| 7,812,043 B2 | 10/2010 | Lau et al. |
| 7,829,558 B2 | 11/2010 | Arnold et al. |
| 7,842,711 B2 | 11/2010 | D'Orchymont et al. |
| 7,902,217 B2 | 3/2011 | Xie et al. |
| 8,008,481 B2 | 8/2011 | Ericsson et al. |
| 8,088,772 B2 | 1/2012 | Garcia et al. |
| 8,129,519 B2 | 3/2012 | Cholody et al. |
| 8,158,647 B2 | 4/2012 | Blaney et al. |
| 8,252,812 B2 | 8/2012 | Hood et al. |
| 8,288,425 B2 | 10/2012 | Edwards et al. |
| 8,304,408 B2 | 11/2012 | Wrasidlo et al. |
| 8,450,340 B2 | 5/2013 | Hood et al. |
| 8,604,052 B2 | 12/2013 | Hood et al. |
| 8,618,128 B1 | 12/2013 | Hood et al. |
| 8,637,508 B2 | 1/2014 | Badiger et al. |
| 8,664,241 B2 | 3/2014 | Hood et al. |
| 8,673,936 B2 | 3/2014 | Hood et al. |
| 8,697,887 B2 | 4/2014 | Hood et al. |
| 8,703,794 B2 | 4/2014 | Hood et al. |
| 8,815,897 B2 | 8/2014 | Hood et al. |
| 8,822,478 B2 | 9/2014 | Hood et al. |
| 8,846,714 B2 | 9/2014 | Hood et al. |
| 8,883,822 B2 | 11/2014 | Hood et al. |
| 8,901,150 B2 | 12/2014 | Hood et al. |
| 8,987,298 B2 | 3/2015 | Hood et al. |
| 9,012,472 B2 | 4/2015 | Hood et al. |
| 9,067,939 B2 | 6/2015 | Hood et al. |
| 9,090,613 B2 | 7/2015 | Hood et al. |
| 2002/0103229 A1 | 8/2002 | Bhagwat et al. |
| 2002/0161022 A1 | 10/2002 | Reich et al. |
| 2003/0199516 A1 | 10/2003 | Moser et al. |
| 2004/0077681 A1 | 4/2004 | Rawlings et al. |
| 2004/0236101 A1 | 11/2004 | Makriyannis et al. |
| 2005/0009894 A1 | 1/2005 | Babin et al. |
| 2005/0026960 A1 | 2/2005 | Kephart et al. |
| 2005/0090529 A1 | 4/2005 | McAlpine et al. |
| 2005/0192262 A1 | 9/2005 | Hagstrom et al. |
| 2005/0208582 A1 | 9/2005 | Ohi et al. |
| 2005/0261339 A1 | 11/2005 | Ohi et al. |
| 2006/0004000 A1 | 1/2006 | D'Orchymont et al. |
| 2006/0014756 A1 | 1/2006 | Edwards et al. |
| 2006/0079564 A1 | 4/2006 | Jansen et al. |
| 2006/0094706 A1 | 5/2006 | Paruch et al. |
| 2006/0111322 A1 | 5/2006 | Reich et al. |
| 2006/0116519 A1 | 6/2006 | Ma et al. |
| 2006/0135589 A1 | 6/2006 | Berdino et al. |
| 2006/0142345 A1 | 6/2006 | Kephart et al. |
| 2006/0167056 A1 | 7/2006 | Rynberg et al. |
| 2006/0264897 A1 | 11/2006 | Lobl |
| 2007/0027140 A1 | 2/2007 | Lau et al. |
| 2007/0060616 A1 | 3/2007 | Bennett et al. |
| 2007/0078147 A1 | 4/2007 | Schumacher et al. |
| 2007/0185187 A1 | 8/2007 | D'Orchymont et al. |
| 2007/0219257 A1 | 9/2007 | Beachy et al. |
| 2007/0282101 A1 | 12/2007 | Ericsson et al. |
| 2008/0004270 A1 | 1/2008 | Gill et al. |
| 2008/0255085 A1 | 10/2008 | Arvidsson et al. |
| 2008/0262205 A1 | 10/2008 | Haar et al. |
| 2009/0005356 A1 | 1/2009 | Blaney et al. |
| 2009/0005377 A1 | 1/2009 | Almansa Rosales et al. |
| 2009/0054397 A1 | 2/2009 | Ohi et al. |
| 2009/0099062 A1 | 4/2009 | Lee et al. |
| 2009/0203690 A1 | 8/2009 | Akritopoulou-Zanze et al. |
| 2009/0286983 A1 | 11/2009 | Almansa Rosales et al. |
| 2010/0298377 A1 | 11/2010 | Aletru et al. |
| 2011/0009353 A1 | 1/2011 | Chen-Kiang et al. |
| 2011/0021467 A1 | 1/2011 | D'Orchymont et al. |
| 2011/0034441 A1 | 2/2011 | Hood et al. |
| 2011/0082144 A1 | 4/2011 | Lau et al. |
| 2011/0178075 A1 | 7/2011 | Xie et al. |
| 2012/0129837 A1 | 5/2012 | Cholody et al. |
| 2012/0277229 A1 | 11/2012 | Bearss et al. |
| 2013/0079329 A1 | 3/2013 | Hood et al. |
| 2014/0194441 A1 | 7/2014 | Kumar |
| 2015/0045379 A1 | 2/2015 | Hood et al. |
| 2015/0150862 A1 | 6/2015 | Hood et al. |
| 2015/0152105 A1 | 6/2015 | Hood et al. |

FOREIGN PATENT DOCUMENTS

| | | |
|---|---|---|
| CN | 1829713 | 9/2006 |
| CN | 101440092 | 5/2009 |
| KZ | 20122 | 1/2010 |
| RU | 2331640 | 8/2008 |
| WO | WO1987005297 | 9/1987 |
| WO | WO1996002537 | 2/1996 |
| WO | WO2001002369 | 1/2001 |
| WO | WO2001053268 | 7/2001 |
| WO | WO2003004488 | 1/2003 |
| WO | WO2003035005 | 5/2003 |
| WO | WO2003035065 | 5/2003 |
| WO | WO2003035644 | 5/2003 |
| WO | WO2003051366 | 6/2003 |
| WO | WO2003070236 | 8/2003 |
| WO | WO2003070706 | 8/2003 |
| WO | WO2003097610 | 11/2003 |
| WO | WO2003101968 | 12/2003 |
| WO | WO2003101993 | 12/2003 |
| WO | WO2004014864 | 2/2004 |
| WO | WO2004031158 | 4/2004 |
| WO | WO2004076450 | 9/2004 |
| WO | WO2005009997 | 2/2005 |
| WO | WO2005014554 | 2/2005 |
| WO | WO2005047266 | 5/2005 |
| WO | WO2005049019 | 6/2005 |
| WO | WO2005092890 | 10/2005 |
| WO | WO2005099703 | 10/2005 |
| WO | WO2005110410 | 11/2005 |
| WO | WO2006001894 | 1/2006 |
| WO | WO2006015124 | 2/2006 |
| WO | WO2006024945 | 3/2006 |
| WO | WO2006054143 | 5/2006 |
| WO | WO2006054151 | 5/2006 |
| WO | WO2006063302 | 6/2006 |
| WO | WO2006063841 | 6/2006 |
| WO | WO2006130673 | 12/2006 |
| WO | WO2007061360 | 5/2007 |
| WO | WO2007107346 | 9/2007 |
| WO | WO2007117465 | 10/2007 |
| WO | WO2008061109 | 5/2008 |
| WO | WO2008071397 | 6/2008 |
| WO | WO2008071398 | 6/2008 |
| WO | WO2008071451 | 6/2008 |
| WO | WO2008124848 | 10/2008 |
| WO | WO2008137408 | 11/2008 |
| WO | WO2008140792 | 11/2008 |
| WO | WO2008147713 | 12/2008 |
| WO | WO2008150914 | 12/2008 |
| WO | WO2008154241 | 12/2008 |
| WO | WO2008156757 | 12/2008 |

(56) References Cited

FOREIGN PATENT DOCUMENTS

| WO | WO2009011850 | | 1/2009 |
|---|---|---|---|
| WO | WO2009016072 | | 2/2009 |
| WO | WO2009061345 | | 5/2009 |
| WO | WO2010107765 | | 9/2010 |
| WO | WO2010111060 | | 9/2010 |
| WO | WO2011011722 | | 1/2011 |
| WO | 2011019648 | * | 2/2011 |
| WO | WO2011019648 | | 2/2011 |
| WO | WO2011050245 | | 4/2011 |
| WO | WO2011079076 | | 6/2011 |
| WO | WO2011084486 | | 7/2011 |
| WO | WO2011123890 | | 10/2011 |
| WO | WO2012068589 | | 5/2012 |
| WO | WO2012104388 | | 8/2012 |
| WO | WO2012129562 | | 9/2012 |
| WO | WO2013024011 | | 2/2013 |

OTHER PUBLICATIONS

Adaimy et al., "Mutation in WNT10A Is Associated with an Autosomal Recessive Ectodermal Dysplasia: The Odonto-onychodermal Dysplasia," *Am. J. Hum. Genet.* (Oct. 2007), 81(4), 821-828.
Anastas and Moon, "WNT signalling pathways as therapeutic targets in cancer," *Nat Rev Cancer*, 13(1):11-26, Jan. 2013.
Andres, "Molecular genetics and animal models in autistic disorder," *Brain Research Bulletin*, (2002), 57(1), 109-119.
Balker and Clevers, "Mining the Wnt pathway for cancer therapeutics," *Nat Rev Drug Discov.*, 5(12):997-1014, Dec. 2006.
Beyer et al., "Extended report: β-catenin is a central mediator of pro-fibrotic Wnt signaling in systemic sclerosis," *Ann Rheum Dis*, 71:761-767, online Feb. 2012.
Biason-Lauber et al., "A WNT4 Mutation Associated with Müllerian-Duct Regression and Virilization in a 46,XX Woman," *N. Engl. J Med.*, (Aug. 2004), 351(8), 792-798.
Blaydon et al., "The gene encoding R-spondin 4 (RSPO4), a secreted protein implicated in Wnt signaling, is mutated in inherited anonychia," *Nat. Genet.*, (Nov. 2006), 38(11), 1245-1247.
Blom et al., "Involvement of the Wnt signaling pathway in experimental and human osteoarthritis: prominent role of Wnt-induced signaling protein 1," *Arthritis Rheum.*, 60(2):501-512, Feb. 2009.
Boyden et al., "High Bone Density Due to a Mutation in LDL-Receptor-Related Protein 5," *N. Engl. J. Med.*, (May 2002), 346(20):1513-1521.
Brack et al., "Increased Wnt signaling during aging alters muscle stem cell fate and increases fibrosis," *Science.*, 317(5839):807-810, Aug. 2007.
Brown et al., "Toxicity and toxicokinetics of the cyclin-dependent kinase inhibitor AG-024322 in cynomolgus monkeys following intravenous infusion," *Cancer Chemother Pharmacol.*, 62(6):1091-1101, Epub May 2008.
Chilosi et al., "The pathogenesis of COPD and IPF: Distinct horns of the same devil?," *Respiratory Research*, 13:3, 2012.
Chou and Talalay, "Quantitative analysis of dose-effect relationships: the combined effects of multiple drugs or enzyme inhibitors," *Advances in Enzyme Regulation* (1984), 22, 27-55.
Chou, "Drug combination studies and their synergy quantification using the Chou-Talalay method," *Cancer Res.*, 70(2):440-446, Jan. 2010.
Chou, "Graphic rule for drug metabolism systems," *Current Drug Metabolism*, (May 2010) 11(4): 369-378.
Christodoulides et al., "WNT10B mutations in human obesity," *Diabetologia*, (2006) 49(4):678-684.
Clevers and Nusse, "Wnt/β-catenin signaling and disease," *Cell* (Jun. 2012), 149(6):1192-1205.
Clevers, "Wnt/beta-catenin signaling in development and disease," *Cell*, (Nov. 2006), 127(3), 469-480.
Corr, "Wnt-beta-catenin signaling in the pathogenesis of osteoarthritis," *Nat Clin Pract Rheumatol.*, 4(10):550-556, Oct. 2008.

D'Alessio et al., "Benzodipyrazoles: a new class of potent CDK2 inhibitors," *Bioorganic & Medicinal Chemistry Letters* (2005), 15(5), 1315-1319.
Dann et al., "Insights into Wnt binding and signaling from the structures of two Frizzled cysteine-rich domains," Nature, (Jul. 2001), 412, pp. 86-90.
Datta et al., "Novel therapeutic approaches for pulmonary fibrosis," *Br J Pharmacol.*, 163(1):141-172, May 2011.
De Ferrari and Inestrosa, "Wnt signaling function in Alzheimer's disease," *Brain Research Reviews*, (2000), 33(1): 1-12.
De Ferrari and Moon, "The ups and downs of Wnt signaling in prevalent neurological disorders," Oncogene, (2006) 25(57): 7545-7553.
De Ferrari et al., "Common genetic variation within the Low-Density Lipoprotein Receptor-Related Protein 6 and late-onset Alzheimer's disease," Proc. Natl. Acad. Sci. USA, (May 2007), 104(22):9434-9439.
Dessalew et al., "3D-QSAR CoMFA and CoMSIA study on benzodipyrazoles as cyclin dependent kinase 2 inhibitors," *Medicinal Chemistry*, (2008), 4(4), 313-321.
Dong et al., "QSAR study of Akt/protein kinase B (PKB) inhibitors using support vector machine," *European Journal of Medicinal Chemistry*, (Oct. 2009), pp. 44(10): 4090-4097.
du Bois, "Strategies for treating idiopathic pulmonary fibrosis," *Nature Reviews Drug Discovery*, 9(2): 129-140 (Feb. 2010).
Egloff et al., "Gastrin-releasing peptide receptor expression in non-cancerous bronchial epithelia is associated with lung cancer: a case-control study," *Respiratory Research*, 13:9, Feb. 2012.
Espada et al., "Wnt signalling and cancer stem cells," *Clin. Transl. Oncol.*, (2009), 11(7), 411-27.
Ewan et al., "A useful approach to identify novel small-molecule inhibitors of Wnt-dependent transcription," *Cancer Res.* (2010), 70(14), 5963-5973.
Florez et al., "TCF7L2 Polymorphisms and Progression to Diabetes in the Diabetes Prevention Program," *N. Engl. J. Med.*, (Jul. 2006), 355(3):241-250.
Freese et al., "Wnt signaling in development and disease," *Neurobiology of Disease*, (2010) 38(2):148-153.
Fujii et al., "An antagonist of dishevelled protein-protein interaction suppresses beta-catenin-dependent tumor cell growth," *Cancer Res.*, 67(2):573-579, Jan. 2007.
Fukuzawa et al., "Beckwith-Wiedemann Syndrome-associated Hepatoblastoma: Wnt Signal Activation Occurs Later in Tumorigenesis in Patients with 11p15.5 Uniparental Disomy," *Pediatric and Developmental Pathology* (2003), 6(4): 299-306.
Giles et al., "Caught up in a Wnt storm: Wnt signaling in cancer," Biochim Biophys Acta., 1653(1):1-24, Jun. 2003.
Handeli and Simon, "A small-molecule inhibitor of Tcf/beta-catenin signaling down-regulates PPARgamma and PPARdelta activities," *Mol Cancer Ther.*, 7(3):521-529, Mar. 2008.
Henderson Jr. et al., "Inhibition of Wnt/beta-catenin/CREB binding protein (CBP) signaling reverses pulmonary fibrosis," *Proc Natl Acad Sci U S A.*, 107(32):14309-14314, Epub Jul. 2010.
Hu et al., "Discovery of indazoles as inhibitors of Tpl2 kinase," *Bioorganic & Medicinal Chemistry Letters*, (Aug. 2011) 21(16): 4758-4761.
Huang et al., "Tankyrase inhibition stabilizes axin and antagonizes Wnt signaling," *Nature*, (Oct. 2009), 461(7264): 614-620.
Huang et al., "Synthesis of 3-(1H-benzimiclazol-2-yl)-5-isoquinolin-4-ylpyrazolo[1,2-b]pyridine, a potent cyclin dependent kinase 1 (CDK1) inhibitor," *Bioorganic & Medicinal Chemistry Letters*, (2007) 17(5): 1243-1245.
Hübner et al., "Standardized quantification of pulmonary fibrosis in histological samples," *Biotechniques*, 44(4):507-511, 514-517, Apr. 2008.
Im et al., "Wnt inhibitors enhance chondrogenesis of human mesenchymal stem cells in a long-term pellet culture," *Biotechnol Lett.*, 33(5):1061-1068, Epub Jan. 2011.
Inestrosa and Toledo, "The role of Wnt signaling in neuronal dysfunction in Alzheimer's Disease," *Mol Neurodegener*, 3:9 doi:10.1186/1750-1326-3-9, 13 pages, Jul. 2008.

(56) References Cited

OTHER PUBLICATIONS

Janssens et al., "The Wnt-dependent signaling pathways as target in oncology drug discovery," *Invest New Drugs.*, 24(4):263-280, Jul. 2006.
Jenkins et al., "Germline mutations in WTX cause a sclerosing skeletal dysplasia but do not predispose to tumorigenesis," *Nat. Genet.* (Jan. 2009), 41(1), 95-100.
Jessen et al., "Peripheral white blood cell toxicity induced by broad spectrum cyclin-dependent kinase inhibitors," *Journal of Applied Toxicology* (Jan. 2007), 27(2), 133-142.
Kanazawa et al., "Association of the Gene Encoding Wingless-Type Mammary Tumor Virus Integration-Site Family Member 5B (WNT5B) with Type 2 Diabetes," *Am. J. Hum. Genet.* (2004), 75(5), 832-843.
Karlberg et al., "Structural basis for the interaction between tankyrase-2 and a potent Wnt-signaling inhibitor," *J. Med. Chem.* (2010), 53(14), 5352-5.
Kibar et al., "Mutations in VANGL1 Associated with Neural-Tube Defects," *N. Engl. J. Med.*, (Apr. 2007), 356(14):1432-1437.
King et al., "BUILD-3: a randomized, controlled trial of bosentan in idiopathic pulmonary fibrosis," *Am J Respir Crit Care Med.*, 184(1):92-99, Epub Apr. 2011.
Kuwajima et al., "Necdin Promotes GABAergic Neuron Differentiation in Cooperation with Dlx Homeodomain Proteins," *Journal of Neuroscience* (May 2006), 26(20), 5383-5392.
Lammi et al., "Mutations in AXIN2 Cause Familial Tooth Agenesis and Predispose to Colorectal Cancer," *Am. J. Hum. Genet.* (2004), 74(5), 1043-1050.
Leyns et al., "Frzb-1 Is a Secreted Antagonist of Wnt Signaling Expressed in the Spemann Organizer," *Cell* (Mar. 1997), 88(6), 747-756.
Li et al., "Artesunate attenuates the growth of human colorectal carcinoma and inhibits hyperactive Wnt/beta-catenin pathway," *Int J Cancer.*, 121(6):1360-1365, Sep. 2007.
Lin et al., "Synthesis and evaluation of pyrazolo[3,4-b]pyridine CDK1 inhibitors as anti-tumor agents," *Bioorganic & Medicinal Chemistry Letters*, (Aug. 2007), 17(15): 4297-4302.
Lories et al., "To Wnt or not to Wnt: the bone and joint health dilemma," *Nat Rev Rheumatol.*, 9(6):328-339, Epub Mar. 2013.
Low et al., "Phenotypic fingerprinting of small molecule cell cycle kinase inhibitors for drug discovery," *Curr Chem Genomics.*, 3:13-21, Mar. 2009.
Lu et al., "Structure-activity relationship studies of small-molecule inhibitors of Wnt response," *Bioorganic & Medicinal Chemistry Letters*, (Jul. 2009), 19(14):3825-3827.
Luo et al., "Fragile X Mental Retardation Protein Regulates Proliferation and Differentiation of Adult Neural Stem/Progenitor Cells," *PLoS Genetics*, (Apr. 2010), 6(4):e1000898, 15 pages.
Luu et at, "Wnt/beta-catenin signaling pathway as a novel cancer drug target," *Curr Cancer Drug Targets.*, 4(8):653-671, Dec. 2004.
Luyten et al., "Wnt signaling and osteoarthritis," *Bone*, 44(4):522-527, Epub Dec. 14, 2008.
MacDonald et al., "Wnt/beta-catenin signaling components, mechanisms, and diseases," *Dev. Cell* (Jul. 2009), 17(1), 9-26.
Mandel et al., "SERKAL Syndrome: An Autosomal-Recessive Disorder Caused by a Loss-of-Function Mutation in WNT4," *Am. J. Hum. Genet.*, (Jan. 2008), 82(1), 39-47.
Mani, et al., "LRP6 Mutation in a Family with Early Coronary Disease and Metabolic Risk Factors," *Science*, (Mar. 2007), 315(5816), 1278-1282.
McBride, et al. "Design and structure-activity relationship of 3-benzimidazol-2-yl-1H-indazoles as inhibitors of receptor tyrosine kinases," *Bioorganic & Medicinal Chemistry Letters* (2006), 16(13), 3595-3599.
Misra et al., "1H-Pyrazolo[3,4-b]pyridine inhibitors of cyclin-dependent kinases: highly potent 2,6-Difuorophenacyl analogues," *Bioorganic & Medicinal Chemistry Letters*, (2003), 13:2405-2408.
Muddassar et al., "Elucidation of binding mode and three dimensional quantitative structure-activity relationship studies of a novel series of protein kinase B/Akt inhibitors ," *Journal of Molecular Modeling*, (2009), 15(2): 183-192.
Niemann et al., "Homozygous WNT3 Mutation Causes Tetra-Amelia in a Large Consanguineous Family," *Am. J. Hum. Genet.* (2004), 74(3), 558-563.
Nishisho et al., "Mutations of chromosome 5q21 genes in FAP and colorectal cancer patients," *Science* (Aug. 1991), 253(5020):665-669.
Nusse, "Wnt signaling in disease and in development," *Cell Res.*, 15(1):28-32, Jan. 2005.
Oates et al., "Increased DNA Methylation at the AXIN1 Gene in a Monozygotic Twin from a Pair Discordant for a Caudal Duplication Anomaly," *Am. J. Hum. Genet.* (2006 ), 79(1), 155-162.
Oduor et al., "Trypanosoma brucei glycogen synthase kinase-3, a target for anti-trypanosomal drug development: a public-private partnership to identify novel leads," *PLoS Negl Trop Dis.*, 5(4):e1017, Apr. 2011.
Okerlund and Cheyette, "Synaptic Wnt signaling—a contributor to major psychiatric disorders?" *J Neurodev Disord.*, (2011) 3(2):162-174.
Polakis, "Wnt signaling and cancer," *Genes Dev.*, 14: 1837-1851, 2000.
Qin et al. "Complexity of the genotype-phenotype correlation in familial exudative vitreoretinopathy with mutations in the LRP5 and/or FZD4 genes," Hum. Mutat. (2005), 26(2), 104-112.
Reya and Clevers, "Wnt signalling in stem cells and cancer," *Nature* 434: 843-850, Apr. 2005.
Richards et al., "Peripheral blood proteins predict mortality in idiopathic pulmonary fibrosis," *Am J Respir Crit Care Med.*, 185(1):67-76, Jan. 2012.
Rivera et al., "An X Chromosome Gene, WTX, Is Commonly Inactivated in Wilms Tumor," *Science*, Feb. 2007), 315(5812):642-645, published online Jan. 4, 2007.
Robitaille et al., "Mutant frizzled-4 disrupts retinal angiogenesis in familial exudative vitreoretinopathy," *Nat. Genet.*, (Sep. 2002), 32(2):326-330.
Ryu et al., "Natural derivatives of curcumin attenuate the Wnt/beta-catenin pathway through down-regulation of the transcriptional coactivator p300," *Biochem Biophys Res Commun.*, 377(4):1304-1308, print Dec. 2008, Epub Nov. 2008.
Salinas, "Wnt signaling in the vertebrate central nervous system: from axon guidance to synaptic function," *Cold Spring Harb Perspect Biol.*, (2012) 4(2). pii: a008003, 15 pages.
Seah et al., "Neuronal Death Resulting from Targeted Disruption of the Snf2 Protein ATRX Is Mediated by p53," *Journal of Neuroscience* (Nov. 2008), 28(47), 12570-12580.
Shih et al., "Pharmacophore modeling and virtual screening to identify potential RET kinase inhibitors," *Bioorg Med Chem Lett.*, 21(15):4490-4497, Epub Jun. 2011.
Shruster et al., "Wnt signaling enhances neurogenesis and improves neurological function after focal ischemic injury," *PLoS One*, (Jul. 2012), 7(7):e40843, 11 pages.
Silva et al, "Advances in Prodrug Design," *Mini-Revs. In Med. Chem.* (2005), 5: 893-914.
Solowiej et al., "Characterizing the Effects of the Juxtamembrane Domain on Vascular Endothelial Growth Factor Receptor-2 Enzymatic Activity, Autophosphorylation, and Inhibition by Axitinib," *Biochemistry*, (2009), 48(29), 7019-7031.
Staines et al., "Cartilage development and degeneration: a Wnt situation," *Cell Biochem Funct.*, 30(8):633-642, Epub Jun. 2012.
Sutherland et al., "A robust high-content imaging approach for probing the mechanism of action and phenotypic outcomes of cell-cycle modulators," *Molecular Cancer Therapeutics*, (Feb. 2011), 10(2):242-254.
Swaney et al., "A novel, orally active LPA(1) receptor antagonist inhibits lung fibrosis in the mouse bleomycin model," *Br J Pharmacol.*, 160(7):1699-1713, Aug. 2010.
Takahashi-Yanaga et al., "Celecoxib-induced degradation of T-cell factors-1 and -4 in human colon cancer cells," *Biochem Biophys Res Commun.*, 377(4):1185-1190, print Dec. 2008, Epub Nov. 2008.

(56) References Cited

OTHER PUBLICATIONS

Tamamura et al., "Developmental regulation of Wnt/beta-catenin signals is required for growth plate assembly, cartilage integrity, and endochondral ossification," *J Biol Chem.*, 280(19):19185-95. Epub. Mar. 2005.
Trujillo et al., "2-(6-Phenyl-1H-indazol-3-yl)-1H-benzo[d]imidazoles: design and synthesis of a potent and isoform selective PKC-zeta inhibitor," *Bioorg Med Chem Lett.*, 19(3):908-911, Epub Dec. 6, 2008.
Ugur et al., "Homozygous WNT10b mutation and complex inheritance in Split-Hand/Foot Malformation," *Hum. Mol. Genet.* (2008), 17(17), 2644-2653.
Vulpetti et al., "Structure-Based Approaches to Improve Selectivity: CDK2-GSK3β Binding Site Analysis," *Journal of Chemical Information and Modeling* (2005), 45(5), 1282-1290.
Wagner et al., "The therapeutic potential of the Wnt signaling pathway in bone disorders," *Curr Mol Pharmacol.*, 4(1):14-25, Jan. 2011.
Walters and Kleeberger, "Mouse models of bleomycin-induced pulmonary fibrosis," *Current Protocols in Pharmacology*, (2008) Chapter 5: Unit 5.46, 1-17.
Wang, et al., "Mutations in X-linked PORCN, a putative regulator of Wnt signaling, cause focal dermal hypoplasia," *Nat. Genet.* (Jul. 2007), 39(7), 836-838.
Wantanabe and Dai, "Winning WNT: race to Wnt signaling inhibitors," *Proc Nail Acad Sci U S A.* 108(15):5929-5930, Epub Mar. 2011.
Weng et al., "Control of Dkk-1 ameliorates chondrocyte apoptosis, cartilage destruction, and subchondral bone deterioration in osteoarthritic knees," *Arthritis Rheum.*, 62(5):1393-1402, May 2010.
Witherington et al., "5-Aryl-pyrazolo[3,4-b]pyridazines: potent inhibitors of glycogen synthase kinase-3 (GSK-3)," *Bioorganic & Medicinal Chemistry Letters*, (May 2003), 13(9):1581-1584.
Woods, S. et al., "Mutations in WNT7A Cause a Range of Limb Malformations, Including Fuhrmann Syndrome and Al-Awadi/Raas-Rothschild/Schinzel Phocomelia Syndrome," *Am. J. Hum. Genet.* (Aug. 2006), 79(2), 402-408.
Yardy and Brewster, "Wnt signalling and prostate cancer," *Prostate Cancer Prostatic Dis*, 8(2):119-126, 2005.
Zhang et al., "Small-molecule synergist of the Wnt/beta-catenin signaling pathway, " *Proc Natl Acad Sci U S A.*, 104(18):7444-7448, Epub Apr. 2007 and correction 104(30):12581, Jul. 2007.
Zhong et al., "Characterization of in vitro and in vivo metabolism of AG-024322, a novel cyclin-dependent kinase (CDK) inhibitor," *Health* (2009), 1(4): 249-262.
Chinese Search Report for application No. 201080044979.2, dated Mar. 14, 2013, 4 pages.
Chinese Search Report for application No. 201080061866.3, dated Aug. 28, 2013, 4 pages.
European Search Report and Written Opinion for App. No. EP12830938.2 dated Mar. 3, 2015, 6 pages.
European Search Report in Application No. 10808586.1, dated Jan. 8, 2013, 8 pages.
European Search Report in Application No. 10808589.5, dated Jan. 8, 2013, 4 pages.
European Search Report in Application No. 10842538, dated Apr. 25, 2013, 5 pages.
International Preliminary Report on Patentability for PCT/US2010/060514 dated Jun. 26, 2012, 9 pages.
International Preliminary Report on Patentability for PCT/US2012/055172 dated Mar. 27, 2014, 8 pages.
International Preliminary Report on Patentability for PCT/US2013/031055, dated Oct. 16, 2014, 9 pages.
International Preliminary Report on Patentability for PCT/US2013/039484, dated Nov. 4, 2014, 7 pages.
International Preliminary Report on Patentability PCT/US2010/044865 dated Feb. 14, 2012, 6 pages.
International Preliminary Report on Patentability PCT/US2010/044872 dated Feb. 14, 2012, 11 pages.
International Search Report and Written Opinion for PCT/US2010/060514, dated Mar. 2, 2011, 11 pages.
International Search Report and Written Opinion for PCT/US2012/055172, dated Nov. 13, 2012,10 pages.
International Search Report and Written Opinion for PCT/US2013/031055, dated May 21, 2013, 14 pages.
International Search Report and Written Opinion for PCT/US2014/10607, dated Aug. 15, 2014, 12 pages.
International Search Report and Written Opinion PCT/US2010/044865 dated Sep. 29, 2010, 2 pages.
International Search Report and Written Opinion PCT/US2010/044872 dated Oct. 5, 2010, 13 pages.
International Search Report for PCT/US2013/039484 dated Dec 5, 2013, 14 pages.

\* cited by examiner

INDAZOLE INHIBITORS OF THE WNT SIGNAL PATHWAY AND THERAPEUTIC USES THEREOF

RELATED APPLICATIONS

Cross-Reference to Related Applications

This application is a continuation application of U.S. application Ser. No. 15/184,553, filed Jun. 16, 2016, which is a continuation application of U.S. application Ser. No. 14/741,645, filed Jun. 17, 2015, which is a continuation application of U.S. application Ser. No. 14/334,005, filed Jul. 17, 2014, which is a continuation application of U.S. application Ser. No. 13/552,188, filed Jul. 18, 2012, which is a continuation of U.S. application Ser. No. 12/852,706, filed Aug. 9, 2010, which claims the benefit of U.S. Provisional Application No. 61/232,603, filed Aug. 10, 2009 and U.S. Provisional Application No. 61/305,459, filed Feb. 17, 2010, all of which are incorporated herein by reference in their entirety.

BACKGROUND OF THE INVENTION

Field of the Invention

This invention relates to inhibitors of one or more proteins in the Wnt pathway, including inhibitors of one or more Wnt proteins, and compositions comprising the same. More particularly, it concerns the use of an indazole compound or salts or analogs thereof, in the treatment of disorders characterized by the activation of Wnt pathway signaling (e.g., cancer, abnormal cellular proliferation, angiogenesis, Alzheimer's disease and osteoarthritis), the modulation of cellular events mediated by Wnt pathway signaling, as well as genetic diseases due to mutations in Wnt signaling components.

Description of the Related Art

Pattern formation is the activity by which embryonic cells form ordered spatial arrangements of differentiated tissues. Speculation on the mechanisms underlying these patterning effects usually centers on the secretion of a signaling molecule that elicits an appropriate response from the tissues being patterned. More recent work aimed at the identification of such signaling molecules implicates secreted proteins encoded by individual members of a small number of gene families.

A longstanding idea in cancer biology is that cancers arise and grow due to the formation of cancer stem cells, which may constitute only a minority of the cells within a tumor but are nevertheless critical for its propagation. Stem cells are appealing as the cell of origin for cancer because of their pre-existing capacity for self-renewal and for unlimited replication. In addition, stem cells are relatively long-lived in comparison to other cells within tissues, providing a greater opportunity to accumulate the multiple additional mutations that may be required to increase the rate of cell proliferation and produce clinically significant cancers. Of particular recent interest in the origin of cancer is the observation that the Wnt signaling pathway, which has been implicated in stem cell self-renewal in normal tissues, upon continuous activation has also been associated with the initiation and growth of many types of cancer. This pathway thus provides a potential link between the normal self-renewal of stem cells and the aberrantly regulated proliferation of cancer stem cells.

The Wnt growth factor family includes more than 10 genes identified in the mouse and at least 7 genes identified in the human. Members of the Wnt family of signaling molecules mediate many important short- and long-range patterning processes during invertebrate and vertebrate development. The Wnt signaling pathway is known for its important role in the inductive interactions that regulate growth and differentiation, and likely also plays important roles in the homeostatic maintenance of post-embryonic tissue integrity. Wnt stabilizes cytoplasmic p-catenin, which stimulates the expression of genes including c-myc, c jun, fra-1, and cyclin Dl. In addition, misregulation of Wnt signaling can cause developmental defects and is implicated in the genesis of several human cancers. More recently, the Wnt pathway has been implicated in the maintenance of stem or progenitor cells in a growing list of adult tissues that now includes skin, blood, gut, prostate, muscle and the nervous system.

Pathological activation of the Wnt pathway is also believed to be the initial event leading to colorectal cancer in over 85% of all sporadic cases in the Western world. Activation of the Wnt pathway has also been extensively reported for hepatocellular carcinoma, breast cancer, ovarian cancer, pancreatic cancer, melanomas, mesotheliomas, lymphomas and leukemias. In addition to cancer, inhibitors of the Wnt pathway can be used for stem cell research or for the treatment of any diseases characterized by aberrant Wnt activation such as diabetic retinopathy, neovascular glaucoma, rheumatoid arthritis, psoriasis as well as mycotic and viral infections and bone and cartilage diseases. As such, it is a therapeutic target that is of great interest to the field.

In addition to cancer, there are many cases of genetic diseases due to mutations in Wnt signaling components. Examples of some of the many diseases are Alzheimer's disease [*Proc. Natl. Acad. Sci. USA* (2007), 104(22), 9434-9], osteoarthritis, polyposis *coli* [*Science* (1991), 253(5020), 665-669], osteoporosis-pseudoglioma syndrome [*N. Engl. J. Med.* (2002), 346(20), 1513-21], familial exudative vitreoretinopathy [*Hum. Mutat.* (2005), 26(2), 104-12], retinal angiogenesis [Nat. Genet. (2002), 32(2), 326-30], early coronary disease [*Science* (2007), 315(5816), 1278-82], tetra-amelia syndrome [*Am. J. Hum. Genet.* (2004), 74(3), 558-63], Müllerian-duct regression and virilization [Engl. J. Med. (2004), 351(8), 792-8], SERKAL syndrome [*Am. J Hum. Genet.* (2008), 82(1), 39-47], diabetes mellitus type 2 [*Am. J Hum. Genet.* (2004), 75(5), 832-43; *N. Engl. J. Med.* (2006), 355(3), 241-50], Fuhrmann syndrome [*Am. J. Hum. Genet.* (2006), 79(2), 402-8], Al-Awadi/Raas-Rothschild/Schinzel phocomelia syndrome [*Am. J. Hum. Genet.* (2006), 79(2), 402-8], odonto-onycho-dermal dysplasia [*Am. J. Hum. Genet.* (2007), 81(4), 821-8], obesity [*Diabetologia* (2006), 49(4), 678-84], split-hand/foot malformation [*Hum. Mol. Genet.* (2008), 17(17), 2644-53], caudal duplication syndrome [*Am. J. Hum. Genet.* (2006), 79(1), 155-62], tooth agenesis [*Am. J. Hum. Genet.* (2004), 74(5), 1043-50], Wilms tumor [*Science* (2007), 315(5812), 642-5], skeletal dysplasia [*Nat. Genet.* (2009), 41(1), 95-100], focal dermal hypoplasia [*Nat. Genet.* (2007), 39(7), 836-8], autosomal recessive anonychia [*Nat. Genet.* (2006), 38(11), 1245-7], neural tube defects [*N. Engl. J. Med.* (2007), 356(14), 1432-7], alpha-thalassemia (ATRX) syndrome [*The Journal of Neuroscience* (2008), 28(47), 12570-12580], fragile X syndrome [*PLoS Genetics* (2010), 6(4), e1000898], ICF syndrome, Angelman syndrome [*Brain Research Bulletin*

(2002), 57(1), 109-119], Prader-Willi syndrome [*Journal of Neuroscience* (2006), 26(20), 5383-5392], Beckwith-Wiedemann Syndrome [*Pediatric and Developmental Pathology* (2003), 6(4), 299-306] and Rett syndrome.

SUMMARY OF THE INVENTION

The present invention makes available methods and reagents, involving contacting a cell with an agent, such as an aromatic compound, in a sufficient amount to antagonize a Wnt activity, e.g., to reverse or control an aberrant growth state or correct an genetic disorder due to mutations in Wnt signaling components.

Some embodiments disclosed herein include Wnt inhibitors containing an indazole core. Other embodiments disclosed herein include pharmaceutical compositions and methods of treatment using these compounds.

One embodiment disclosed herein includes a compound having the structure of formula I:

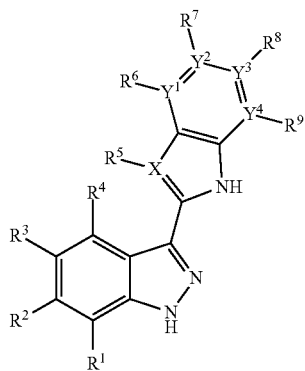

I as well as prodrugs and pharmaceutically acceptable salts thereof.

In some embodiments of formula (I):

$R^1$, $R^2$, $R^4$, $R^6$, $R^7$, $R^8$ and $R^9$ are independently selected from the group consisting of H, $C_{1-9}$ alkyl, halide, —$CF_3$, —($C_{1-9}$ alkyl)$_n$carbocyclyl$R^{13}$, —($C_{1-9}$ alkyl)$_n$heterocyclyl$R^{13}$, —($C_{1-9}$ alkyl)$_n$aryl$R^{13}$, —($C_{1-9}$ alkyl)$_n$heteroaryl$R^{13}$, —($C_{1-9}$ alkyl)$_n$OR$^{10}$, —($C_{1-9}$ alkyl)$_n$SR$^{10}$, —($C_{1-9}$ alkyl)$_n$S(=O)R$^{11}$, —($C_{1-9}$ alkyl)$_n$SO$_2$R$^{10}$, —($C_{1-9}$ alkyl)$_n$N(R$^{10}$)SO$_2$R$^{10}$, —($C_{1-9}$ alkyl)$_n$SO$_2$N(R$^{10}$)$_2$, —($C_{1-9}$ alkyl)$_n$N(R$^{10}$)$_2$, —($C_{1-9}$ alkyl)$_n$N(R$^{10}$)C(=A)N(R$^{10}$)$_2$, —($C_{1-9}$ alkyl)$_n$NR$^{10}$C(=O)OR$^{10}$, —($C_{1-9}$ alkyl)$_n$C(=A)N(R$^{10}$)$_2$, —($C_{1-9}$ alkyl)$_n$N(R$^{10}$)C(=A)R$^{10}$, —($C_{1-9}$ alkyl)$_n$OC(=O)N(R$^{10}$)$_2$, —NO$_2$, —CN, —($C_{1-9}$ alkyl)$_n$CO$_2$R$^{10}$ and —($C_{1-9}$ alkyl)$_n$C(=A)R$^{10}$;

$R^3$ is selected from the group consisting of —NRS(=O)R$^{14}$, —($C_{1-9}$alkyl)R$^{14}$, -carbocyclylR$^{14}$R$^{15}$, -heterocyclylR$^{14}$R$^{15}$, -arylR$^{14}$R$^{15}$ or -heteroarylR$^{14}$R$^{15}$;

alternatively, one of each $R^1$ and $R^2$, $R^2$ and $R^3$, $R^3$ and $R^4$, $R^6$ and $R^7$, $R^7$ and $R^8$ or $R^8$ and $R^9$ are taken together to form a ring which is selected from the group consisting of aryl, heteroaryl,

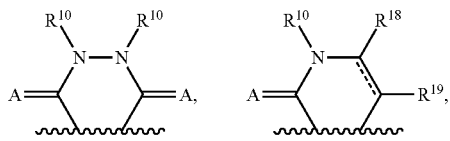

-continued

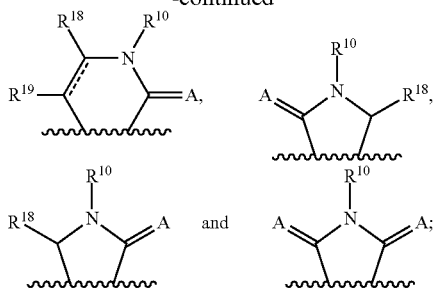

wherein each bond represented by a dashed and solid line represents a bond selected from the group consisting of a single bond and a double bond;

each $R^{10}$ is independently selected from the group consisting of H, —$C_{1-9}$ alkyl, —$CF_3$, —($C_{1-9}$ alkyl)$_n$carbocyclyl, —($C_{1-9}$ alkyl)$_n$heterocyclyl, —($C_{1-9}$ alkyl)$_n$aryl and —($C_{1-9}$ alkyl)$_n$heteroaryl;

each $R^{11}$ is independently selected from the group consisting of —$C_{1-9}$ alkyl, —$CF_3$, —($C_{1-9}$ alkyl)$_n$carbocyclyl, —($C_{1-9}$ alkyl)$_n$heterocyclyl, —($C_{1-9}$ alkyl)$_n$aryl and —($C_{1-9}$ alkyl)$_n$heteroaryl;

each $R^{12}$ is independently selected from the group consisting of CN, —OR$^{10}$ and R$^{10}$;

$R^{13}$ is 1-5 substituents each selected from the group consisting of H, $C_{1-9}$ alkyl, halide, —$CF_3$, carbocyclylR$^{13}$, heterocyclylR$^{13}$, arylR$^{13}$, heteroarylR$^{13}$, —($C_{1-9}$ alkyl)$_n$OR$^{10}$, —($C_{1-9}$ alkyl)$_n$SR$^{10}$, —($C_{1-9}$ alkyl)$_n$S(=O)R$^{11}$, —($C_{1-9}$ alkyl)$_n$SO$_2$R$^{10}$, —($C_{1-9}$ alkyl)$_n$N(R$^{10}$)SO$_2$R$^{10}$, —($C_{1-9}$ alkyl)$_n$SO$_2$N(R$^{10}$)$_2$, —($C_{1-9}$ alkyl)$_n$N(R$^{10}$)$_2$, —($C_{1-9}$ alkyl)$_n$N(R$^{10}$)C(=A)N(R$^{10}$)$_2$, —($C_{1-9}$ alkyl)$_n$NR$^{10}$C(=O)OR$^{10}$, —($C_{1-9}$ alkyl)$_n$C(=A)N(R$^{10}$)$_2$, —($C_{1-9}$ alkyl)$_n$N(R$^{10}$)C(=A)R$^{10}$, —($C_{1-9}$ alkyl)$_n$OC(=O)N(R$^{10}$)$_2$, —NO$_2$, —CN, —($C_{1-9}$ alkyl)$_n$CO$_2$R$^{10}$ and —($C_{1-9}$ alkyl)$_n$C(=A)R$^{10}$;

$R^{14}$ is selected from the group consisting of —NR$^{10}$C(=A)R, —NR$^{10}$S(=O)R$^{11}$, —NR$^{10}$SO$_2$R$^{10}$, —NR$^{10}$C(=O)N(R$^{16}$)$_2$, —NR$^{10}$C(=S)N(R$^{10}$)$_2$, —NR$^{10}$C(=NR$^{12}$)N(R$^{10}$)$_2$, —N(R$^{16}$)$_2$, —C(=O)NR$^{10}$R$^{17}$, —C(=S)N(R$^{10}$)$_2$, —C(=NR$^{12}$)N(R$^{10}$)$_2$, —OC(=A)R$^{10}$, —C(=A)R$^{10}$, —NR$^{10}$C(=A)OR$^{10}$ and —OC(=A)NR$^{10}$R$^{10}$;

$R^{15}$ is 1-5 substituents each selected from the group consisting of H, $C_{1-9}$ alkyl, halide, —$CF_3$, carbocyclylR$^{13}$, heterocyclylR$^{13}$, arylR$^{13}$, heteroarylR$^{13}$, —($C_{1-9}$ alkyl)$_n$OR$^{10}$, —($C_{1-9}$ alkyl)$_n$SR$^{10}$, —($C_{1-9}$ alkyl)$_n$S(=O)R$^{11}$, —($C_{1-9}$ alkyl)$_n$SO$_2$R$^{10}$, —($C_{1-9}$ alkyl)$_n$N(R$^{10}$)SO$_2$R$^{10}$, —($C_{1-9}$ alkyl)$_n$SO$_2$N(R$^{10}$)$_2$, —($C_{1-9}$ alkyl)$_n$N(R$^{10}$)$_2$, —($C_{1-9}$ alkyl)$_n$N(R$^{10}$)C(=A)N(R$^{10}$)$_2$, —($C_{1-9}$ alkyl)$_n$NR$^{10}$C(=O)OR$^{10}$, —($C_{1-9}$ alkyl)$_n$C(=A)N(R$^{10}$)$_2$, —($C_{1-9}$ alkyl)$_n$N(R$^{10}$)C(=A)R$^{10}$, —($C_{1-9}$ alkyl)$_n$OC(=O)N(R$^{10}$)$_2$, —NO$_2$, —CN, —($C_{1-9}$ alkyl)$_n$CO$_2$R$^{10}$ and —($C_{1-9}$ alkyl)$_n$C(=A)R$^{10}$;

$R^{16}$ is —$C_{1-9}$ alkyl;

each $R^{17}$ is independently selected from the group consisting of -heterocyclylR$^{13}$, —($C_{1-9}$ alkyl)heterocyclylR$^{13}$ and —($C_{1-9}$ alkyl)carbocyclylR$^{13}$;

$R^{18}$ and $R^{19}$ are independently selected from the group consisting of H, $C_{1-9}$ alkyl, halide, —($C_{1-9}$ alkyl)$_n$carbocyclylR$^{13}$, —($C_{1-9}$ alkyl)$_n$heterocyclylR$^{13}$, —($C_{1-9}$ alkyl)$_n$arylR$^{13}$, —($C_{1-9}$ alkyl)$_n$heteroarylR$^{13}$, —($C_{1-9}$ alkyl)$_n$OR$^{10}$, —($C_{1-9}$ alkyl)$_n$SR$^{10}$, —($C_{1-9}$ alkyl)$_n$S(=O)R$^{11}$, —($C_{1-9}$ alkyl)$_n$SO$_2$R$^{10}$, —($C_{1-9}$ alkyl)$_n$N(R$^{10}$)SO$_2$R$^{10}$, —($C_{1-9}$ alkyl)$_n$SO$_2$N(R$^{10}$)$_2$, —($C_{1-9}$ alkyl)$_n$N(R$^{10}$)$_2$, —($C_{1-9}$ alkyl)$_n$N(R$^{10}$)C(=A)N(R$^{10}$)$_2$, —($C_{1-9}$ alkyl)$_n$C(=A)N(R$^{10}$)$_2$, —($C_{1-9}$ alkyl)$_n$N(R$^{10}$)C(=A)R$^{10}$, —NO$_2$, —CN, —($C_{1-9}$ alkyl)$_n$CO$_2$R$^{10}$ and —($C_{1-9}$ alkyl)$_n$C(=A)R$^{10}$;

alternatively, $R^{18}$ and $R^{19}$ are taken together to form a ring which is selected from the group consisting of benzene and pyridine;

each A is independently selected from O, S and $NR^{12}$;

X is nitrogen and $R^5$ is absent;

$Y^1$, $Y^2$, $Y^3$ and $Y^4$ are independently selected from the group consisting of carbon and nitrogen with the proviso that at least one of $Y^1$, $Y^2$, $Y^3$ and $Y^4$ are nitrogen;

if $Y^1$ is nitrogen then $R^6$ is absent;
if $Y^2$ is nitrogen then $R^7$ is absent;
if $Y^3$ is nitrogen then $R^8$ is absent;
if $Y^4$ is nitrogen then $R^9$ is absent; and
each n is 0 or 1.

In other embodiments of formula (I):

$R^1$, $R^2$, $R^3$, $R^4$, $R^5$, $R^6$, $R^7$, $R^8$ and $R^9$ are independently selected from the group consisting of H, $C_{1-9}$ alkyl, halide, $-CF_3$, $-(C_{1-9} \text{ alkyl})_n\text{carbocyclyl}R^{12}$, $-(C_{1-9} \text{ alkyl})_n\text{heterocyclyl}R^{12}$, $-(C_{1-9} \text{ alkyl})_n\text{aryl}R^{12}$, $-(C_{1-9} \text{ alkyl})_n\text{heteroaryl}R^{12}$, $-(C_{1-9} \text{ alkyl})_nOR^9$, $-(C_{1-9} \text{ alkyl})_nSR^9$, $-(C_{1-9} \text{ alkyl})_nS(=O)R^{10}$, $-(C_{1-9} \text{ alkyl})_nSO_2R^9$, $-(C_{1-9} \text{ alkyl})_nN(R^9)S(=O)R^{10}$, $-(C_{1-9} \text{ alkyl})_nN(R^9)SO_2R^9$, $-(C_{1-9} \text{ alkyl})_nSO_2N(R^9)_2$, $-(C_{1-9} \text{ alkyl})_nN(R^9)_2$, $-(C_{1-9} \text{ alkyl})_nN(R^9)C(=A)N(R^9)_2$, $-(C_{1-9} \text{ alkyl})_nNR^9C(=O)OR^9$, $-(C_{1-9} \text{ alkyl})_nC(=A)N(R^9)_2$, $-(C_{1-9} \text{ alkyl})_nN(R^9)C(=A)R^9$, $-(C_{1-9} \text{ alkyl})_nOC(=O)NR^9R^9$, $-NO_2$, $-CN$, $-(C_{1-9} \text{ alkyl})_nCO_2R^9$ and $-(C_{1-9} \text{ alkyl})_nC(=A)R^9$;

alternatively, one of each $R^1$ and $R^2$, $R^2$ and $R^3$, $R^3$ and $R^4$, $R^6$ and $R^7$, $R^7$ and $R^8$ or $R^8$ and $R^9$ are taken together to form a ring which is selected from the group consisting of aryl, heteroaryl,

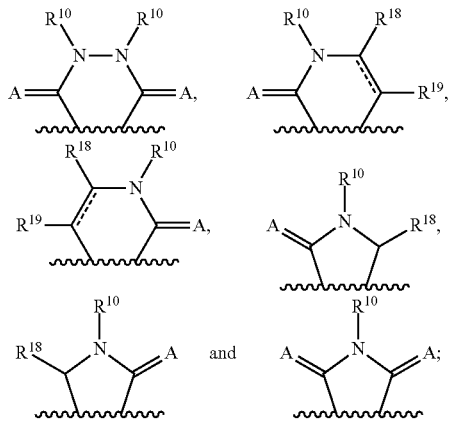

wherein each bond represented by a dashed and solid line represents a bond selected from the group consisting of a single bond and a double bond;

each $R^{10}$ is independently selected from the group consisting of H, $-C_{1-9}$ alkyl, $-CF_3$, $-(C_{1-9} \text{ alkyl})_n\text{carbocyclyl}$, $-(C_{1-9} \text{ alkyl})_n\text{heterocyclyl}$, $-(C_{1-9} \text{ alkyl})_n\text{aryl}$ and $-(C_{1-9} \text{ alkyl})_n\text{heteroaryl}$;

each $R^{10}$ is independently selected from the group consisting of $-C_{1-9}$ alkyl, $-CF_3$, $-(C_{1-9} \text{ alkyl})_n\text{carbocyclyl}$, $-(C_{1-9} \text{ alkyl})_n\text{heterocyclyl}$, $-(C_{1-9} \text{ alkyl})_n\text{aryl}$ and $-(C_{1-9} \text{ alkyl})_n\text{heteroaryl}$;

each $R^{12}$ is independently selected from the group consisting of CN, $-OR^{10}$ and $R^{10}$;

$R^{13}$ is 1-5 substituents each selected from the group consisting of H, $C_{1-9}$ alkyl, halide, $-CF_3$, carbocyclyl$R^{12}$, heterocyclyl$R^{12}$, aryl$R^{12}$, heteroaryl$R^{12}$, $-(C_{1-9} \text{ alkyl})_nOR^9$, $(C_{1-9} \text{ alkyl})_nSR^9$, $-(C_{1-9} \text{ alkyl})_nS(=O)R^{10}$, $-(C_{1-9} \text{ alkyl})_nSO_2R^9$, $-(C_{1-9} \text{ alkyl})_nN(R^9)SO_2R^9$, $(C_{1-9} \text{ alkyl})_nSO_2N(R^9)_2$, $-(C_{1-9} \text{ alkyl})_nN(R^9)_2$, $-(C_{1-9} \text{ alkyl})_nN(R^9)C(=A)N(R^9)_2$, $-(C_{1-9} \text{ alkyl})_nC(=A)N(R^9)_2$, $-(C_{1-9} \text{ alkyl})_nNR^9C(=O)OR^9$, $-(C_{1-9} \text{ alkyl})_nN(R^9)C(=A) R^9$, $-(C_{1-9} \text{ alkyl})_nOC(=O)N(R^9)_2$, $-NO_2$, $-CN$, $-(C_{1-9} \text{ alkyl})_nCO_2R^9$ and $-(C_{1-9} \text{ alkyl})_nC(=A)R^9$;

$R^{18}$ and $R^{19}$ are independently selected from the group consisting of H, $C_{1-9}$ alkyl, halide, $-(C_{1-9} \text{ alkyl})_n\text{carbocyclyl}R^{13}$, $-(C_{1-9} \text{ alkyl})_n\text{heterocyclyl}R^{13}$, $-(C_{1-9} \text{ alkyl})_n\text{aryl}R^{13}$, $-(C_{1-9} \text{ alkyl})_n\text{heteroaryl}R^{13}$, $-(C_{1-9} \text{ alkyl})_nOR^{10}$, $-(C_{1-9} \text{ alkyl})_nSR^{10}$, $-(C_{1-9} \text{ alkyl})_nS(=O)R^{10}$, $-(C_{1-9} \text{ alkyl})_nSO_2R^{10}$, $-(C_{1-9} \text{ alkyl})_nN(R^{10})SO_2R^{10}$, $-(C_{1-9} \text{ alkyl})_nSO_2N(R^{10})_2$, $-(C_{1-9} \text{ alkyl})_nN(R^{10})_2$, $-(C_{1-9} \text{ alkyl})_nN(R^{10})C(=A)N(R^{10})_2$, $-(C_{1-9} \text{ alkyl})_nC(=A)N(R^{10})_2$, $-(C_{1-9} \text{ alkyl})_nN(R^{10})C(=A)R^{10}$, $-NO_2$, $-CN$, $-(C_{1-9} \text{ alkyl})_nCO_2R^{10}$ and $-(C_{1-9} \text{ alkyl})_nC(=A)R^{10}$;

alternatively, $R^{18}$ and $R^{19}$ are taken together to form a ring which is selected from the group consisting of benzene and pyridine;

each A is independently selected from O, S and $NR^{12}$;

X is carbon;

$Y^1$, $Y^2$, $Y^3$ and $Y^4$ are independently selected from the group consisting of carbon and nitrogen with the proviso that at least one of $Y^1$, $Y^2$, $Y^3$ and $Y^4$ are nitrogen;

if $Y^1$ is nitrogen then $R^6$ is absent;
if $Y^2$ is nitrogen then $R^7$ is absent;
if $Y^3$ is nitrogen then $R^8$ is absent;
if $Y^4$ is nitrogen then $R^9$ is absent; and
each n is 0 or 1, or a pharmaceutically acceptable salt or pro-drug thereof.

Some embodiments include stereoisomers and pharmaceutically acceptable salts of a compound of general formula (I).

Some embodiments include pro-drugs of a compound of general formula (I).

Some embodiments of the present invention include pharmaceutical compositions comprising a compound of general formula (I) and a pharmaceutically acceptable carrier.

Other embodiments disclosed herein include methods of inhibiting one or more members of the Wnt pathway, including one or more Wnt proteins by administering to a subject affected by a disorder or disease in which aberrant Wnt signaling is implicated, such as cancer and other diseases associated with abnormal angiogenesis, cellular proliferation, cell cycling and mutations in Wnt signaling components, a compound according to any of the above formulas. Accordingly, the compounds and compositions provided herein can be used to treat cancer, to reduce or inhibit angiogenesis, to reduce or inhibit cellular proliferation and correct an genetic disorder due to mutations in Wnt signaling components. Non-limiting examples of diseases which can be treated with the compounds and compositions provided herein include a variety of cancers, diabetic retinopathy, neovascular glaucoma, rheumatoid arthritis, psoriasis, mycotic and viral infections, osteochondrodysplasia, Alzheimer's disease, osteoarthritis, polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome and Rett syndrome.

Another embodiment disclosed herein includes a pharmaceutical composition that has a compound according to any of the above formulas and a pharmaceutically acceptable carrier, diluent, or excipient.

Some embodiments of the present invention include methods to prepare a compound of general formula (I).

It is to be understood that both the foregoing general description and the following detailed description are exemplary and explanatory only and are not restrictive of the invention, as claimed.

DETAILED DESCRIPTION OF THE INVENTION

Compositions and methods for inhibiting one or more members of the Wnt pathway, including one or more Wnt proteins would be of tremendous benefit. Certain embodiments provide such compositions and methods.

Some embodiments relate to a method for treating a disease such as cancers, diabetic retinopathy, neovascular glaucoma, rheumatoid arthritis, psoriasis, mycotic and viral infections, osteochondrodysplasia, Alzheimer's disease, osteoarthritis, polyposis *coli*, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome and Rett syndrome.

In some embodiments, pharmaceutical compositions are provided that are effective for treatment of a disease of an animal, e.g., a mammal, caused by the pathological activation or mutations of the Wnt pathway. The composition includes a pharmaceutically acceptable carrier and a Wnt pathway inhibitor as described herein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

In this specification and in the claims, the following terms have the meanings as defined. As used herein, "alkyl" means a branched, or straight chain chemical group containing only carbon and hydrogen, such as methyl, isopropyl, isobutyl, sec-butyl and pentyl. Alkyl groups can either be unsubstituted or substituted with one or more substituents, e.g., halogen, alkoxy, acyloxy, amino, amido, cyano, nitro, hydroxyl, mercapto, carboxy, carbonyl, benzyloxy, aryl, heteroaryl, or other functionality that may be suitably blocked, if necessary for purposes of the invention, with a protecting group. Alkyl groups can be saturated or unsaturated (e.g., containing —C═C— or —C≡C— subunits), at one or several positions. Typically, alkyl groups will comprise 1 to 9 carbon atoms, preferably 1 to 6, and more preferably 1 to 4 carbon atoms.

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. Carbocyclyl groups can either be unsubstituted or substituted with one or more substituents, e.g., halogen, alkoxy, acyloxy, amino, amido, cyano, nitro, hydroxyl, mercapto, carboxy, carbonyl, benzyloxy, aryl, heteroaryl, or other functionality that may be suitably blocked, if necessary for purposes of the invention, with a protecting group. Typically, carbocyclyl groups will comprise 3 to 10 carbon atoms, preferably 3 to 6.

As used herein, "lower alkyl" means a subset of alkyl, and thus is a hydrocarbon substituent, which is linear, or branched. Preferred lower alkyls are of 1 to about 4 carbons, and may be branched or linear. Examples of lower alkyl include butyl, propyl, isopropyl, ethyl, and methyl. Likewise, radicals using the terminology "lower" refer to radicals preferably with 1 to about 4 carbons in the alkyl portion of the radical.

As used herein, "amido" means a H—CON— or alkyl-CON—, carbocyclyl-CON—, aryl-CON—, heteroaryl-CON— or heterocyclyl-CON group wherein the alkyl, carbocyclyl, aryl or heterocyclyl group is as herein described.

As used herein, "aryl" means an aromatic radical having a single-ring (e.g., phenyl) or multiple condensed rings (e.g., naphthyl or anthryl) with only carbon atoms present in the ring backbone. Aryl groups can either be unsubstituted or substituted with one or more substituents, e.g., amino, cyano, hydroxyl, lower alkyl, haloalkyl, alkoxy, nitro, halo, mercapto, and other substituents. A preferred carbocyclic aryl is phenyl.

As used herein, the term "heteroaryl" means an aromatic radical having one or more heteroatom(s) (e.g., N, O, or S) in the ring backbone and may include a single ring (e.g., pyridine) or multiple condensed rings (e.g., quinoline). Heteroaryl groups can either be unsubstituted or substituted with one or more substituents, e.g., amino, cyano, hydroxyl, lower alkyl, haloalkyl, alkoxy, nitro, halo, mercapto, and other substituents. Examples of heteroaryl include thienyl, pyrridyl, furyl, oxazolyl, oxadiazolyl, pyrollyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl and others.

In these definitions it is clearly contemplated that substitution on the aryl and heteroaryl rings is within the scope of certain embodiments. Where substitution occurs, the radical is called substituted aryl or substituted heteroaryl. Preferably one to three and more preferably one or two substituents occur on the aryl ring. Though many substituents will be useful, preferred substituents include those commonly found in aryl compounds, such as alkyl, cycloalkyl, hydroxy, alkoxy, cyano, halo, haloalkyl, mercapto and the like.

As used herein, "amide" includes both RNR'CO— (in the case of R=alkyl, alkaminocarbonyl-) and RCONR'— (in the case of R=alkyl, alkyl carbonylamino-).

As used herein, the term "ester" includes both ROCO— (in the case of R=alkyl, alkoxycarbonyl-) and RCOO— (in the case of R=alkyl, alkylcarbonyloxy-).

As used herein, "acyl" means an H—CO— or alkyl-CO—, carbocyclyl-CO-aryl-CO—, heteroaryl-CO— or heterocyclyl-CO— group wherein the alkyl, carbocyclyl, aryl or heterocyclyl group is as herein described. Preferred acyls contain a lower alkyl. Exemplary alkyl acyl groups include formyl, acetyl, propanoyl, 2-methylpropanoyl, t-butylacetyl, butanoyl and palmitoyl.

As used herein, "halo or halide" is a chloro, bromo, fluoro or iodo atom radical. Chloro, bromo and fluoro are preferred halides. The term "halo" also contemplates terms sometimes referred to as "halogen", or "halide".

As used herein, "haloalkyl" means a hydrocarbon substituent, which is linear or branched or cyclic alkyl, alkenyl or alkynyl substituted with chloro, bromo, fluoro or iodo atom(s). Most preferred of these are fluoroalkyls, wherein one or more of the hydrogen atoms have been substituted by fluoro. Preferred haloalkyls are of 1 to about 3 carbons in length, more preferred haloalkyls are 1 to about 2 carbons, and most preferred are 1 carbon in length. The skilled artisan will recognize then that as used herein, "haloalkylene" means a diradical variant of haloalkyl, such diradicals may act as spacers between radicals, other atoms, or between the parent ring and another functional group.

As used herein, "heterocyclyl" means a cyclic ring system comprising at least one heteroatom in the ring system backbone. Heterocyclyls may include multiple fused rings. Heterocyclyls may have any degree of saturation provided that at least one ring in the ring system is not aromatic. Heterocyclyls may be substituted or unsubstituted with one or more substituents, e.g., halogen, alkoxy, acyloxy, amino, amido, cyano, nitro, hydroxyl, mercapto, carboxy, carbonyl, benzyloxy, aryl, heteroaryl, and other substituents, and are attached to other groups via any available valence, preferably any available carbon or nitrogen. More preferred heterocycles are of 5-7 members. In six membered monocyclic heterocycles, the heteroatom(s) are selected from one up to three of O, N or S, and wherein when the heterocycle is five membered, preferably it has one or two heteroatoms selected from O, N, or S.

As used herein, "substituted amino" means an amino radical which is substituted by one or two alkyl, cycloalkyl, aryl, heteroaryl or heterocyclyl groups, wherein the alkyl, aryl, heteroaryl or heterocyclyl are defined as above.

As used herein, "substituted thiol" means RS— group wherein R is an alkyl, an aryl, heteroaryl or a heterocyclyl group, wherein the alkyl, cycloalkyl, aryl, heteroaryl or heterocyclyl are defined as above.

As used herein, "sulfonyl" means an alkyl$SO_2$, aryl$SO_2$, heteroaryl$SO_2$, carbocyclyl$SO_2$, or heterocyclyl-$SO_2$ group wherein the alkyl, carbocyclyl, aryl, heteroaryl or heterocyclyl are defined as above.

As used herein, "sulfamido" means an alkyl-N—S(O)$_2$N—, aryl-NS(O)$_2$N-heteroaryl-NS(O)$_2$N—, carbocyclyl-NS(O)$_2$N or heterocyclyl-NS(O)$_2$N— group wherein the alkyl, carbocyclyl, aryl, heteroaryl or heterocyclyl group is as herein described.

As used herein, "sulfonamido" means an alkyl-S(O)$_2$N—, aryl-S(O)$_2$N—, heteroaryl-S(O)$_2$N—, carbocyclyl-S(O)$_2$N- or heterocyclyl-S(O)$_2$N— group wherein the alkyl, carbocyclyl, aryl, heteroaryl or heterocyclyl group is as herein described.

As used herein, "ureido" means an alkyl-NCON—, aryl-NCON—, heteroaryl-NCON—, carbocyclyl-NCON— or heterocyclyl-NCON— group wherein the alkyl, carbocyclyl, aryl, heteroaryl or heterocyclyl group is as herein described.

As used herein, when two groups are indicated to be "linked" or "bonded" to form a "ring," it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions, and it is within the purview of the skilled artisan to both envision such rings and the methods of their formations. Preferred are rings having from 3-7 members, more preferably 5 or 6 members. As used herein the term "ring" or "rings" when formed by the combination of two radicals refers to heterocyclic, carbocyclic, aryl, or heteroaryl rings.

The skilled artisan will recognize that some structures described herein may be resonance forms or tautomers of compounds that may be fairly represented by other chemical structures, even when kinetically, the artisan recognizes that such structures are only a very small portion of a sample of such compound(s). Such compounds are clearly contemplated within the scope of this invention, though such resonance forms or tautomers are not represented herein.

The compounds provided herein may encompass various stereochemical forms. The compounds also encompasses diastereomers as well as optical isomers, e.g. mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound.

The term "administration" or "administering" refers to a method of giving a dosage of a compound or pharmaceutical composition to a vertebrate or invertebrate, including a mammal, a bird, a fish, or an amphibian, where the method is, e.g., intrarespiratory, topical, oral, intravenous, intraperitoneal, intramuscular, buccal, rectal, sublingual. The preferred method of administration can vary depending on various factors, e.g., the components of the pharmaceutical composition, the site of the disease, the disease involved, and the severity of the disease.

A "diagnostic" as used herein is a compound, method, system, or device that assists in the identification and characterization of a health or disease state. The diagnostic can be used in standard assays as is known in the art.

The term "mammal" is used in its usual biological sense. Thus, it specifically includes humans, cattle, horses, dogs, and cats, but also includes many other species.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (2006); *Goodman and Gilman's: The Pharmacological Basis of Therapeutics,* 11*th Ed.,* The McGraw-Hill Companies.

The term "pharmaceutically acceptable salt" refers to salts that retain the biological effectiveness and properties of the compounds of the preferred embodiments and, which are not biologically or otherwise undesirable. In many cases, the compounds of the preferred embodiments are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in World Patent Publication 87/05297, Johnston et al., published Sep. 11, 1987 (incorporated by reference herein).

"Solvate" refers to the compound formed by the interaction of a solvent and a Wnt pathway inhibitor, a metabolite, or salt thereof. Suitable solvates are pharmaceutically acceptable solvates including hydrates.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

By "therapeutically effective amount" or "pharmaceutically effective amount" is typically one which is sufficient to achieve the desired effect and may vary according to the nature and severity of the disease condition, and the potency of the compound. It will be appreciated that different concentrations may be employed for prophylaxis than for treatment of an active disease. This amount can further depend upon the patient's height, weight, sex, age and medical history.

A therapeutic effect relieves, to some extent, one or more of the symptoms of the disease, and includes curing a disease. "Curing" means that the symptoms of active disease are eliminated. However, certain long-term or permanent effects of the disease may exist even after a cure is obtained (such as extensive tissue damage).

"Treat," "treatment," or "treating," as used herein refers to administering a pharmaceutical composition for therapeutic purposes. The term "therapeutic treatment" refers to administering treatment to a patient already suffering from a disease thus causing a therapeutically beneficial effect, such as ameliorating existing symptoms, preventing additional symptoms, ameliorating or preventing the underlying metabolic causes of symptoms, postponing or preventing the further development of a disorder and/or reducing the severity of symptoms that will or are expected to develop.

Compounds

The compounds and compositions described herein can be used as anti-proliferative agents, e.g., anti-cancer and anti-angiogenesis agents, and as inhibitors of the Wnt signaling pathway, e.g., for treating diseases or disorders associated with aberrant Wnt signaling. In addition, the compounds can be used as inhibitors of one or more kinases, kinase receptors, or kinase complexes (e.g., VEGF, CHK-1, CLK, HIPK, Abl, JAK and/or CDK complexes). Such compounds and compositions are also useful for controlling cellular proliferation, differentiation, and/or apoptosis.

Some embodiments of the present invention include compounds, salts, pharmaceutically acceptable salts or pro-drug thereof of formula (Ia):

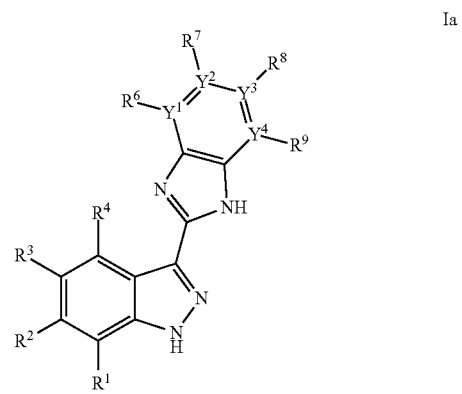

In some embodiments, $R^1$, $R^2$, $R^4$, $R^6$, $R^{7'}$ $R^8$ and $R^9$ are independently selected from the group consisting of H, $C_{1-9}$ alkyl, halide, $-CF_3$, $-(C_{1-9}$ alkyl$)_n$carbocyclyl$R^{13}$, $-(C_{1-9}$ alkyl$)_n$heterocyclyl$R^{13}$, $-(C_{1-9}$ alkyl$)_n$aryl$R^{13}$, $-(C_{1-9}$ alkyl$)_n$heteroaryl$R^{13}$, $-(C_{1-9}$ alkyl$)_n$OR$^{10}$, $-(C_{1-9}$ alkyl$)_n$SR$^{10}$, $-(C_{1-9}$ alkyl$)_n$S(=O)$R^{11}$, $-(C_{1-9}$ alkyl$)_n$SO$_2R^{10}$, $-(C_{1-9}$ alkyl$)_n$N(R$^{10}$)SO$_2R^{10}$, $-(C_{1-9}$ alkyl$)_n$SO$_2$N(R$^{10}$)$_2$, $-(C_{1-9}$ alkyl$)_n$N(R$^{10}$)$_2$, $-(C_{1-9}$ alkyl$)_n$N(R$^{10}$)C(=A)N(R$^{10}$)$_2$, $-(C_{1-9}$ alkyl$)_n$C(=A)N(R$^{10}$)$_2$, $-(C_{1-9}$ alkyl$)_n$N(R$^{10}$)C(=A)R$^{10}$, $-NO_2$, $-CN$, $-(C_{1-9}$ alkyl$)_n$CO$_2R^{10}$ and $-(C_{1-9}$ alkyl$)_n$C(=A)R$^{10}$.

In some embodiments, $R^3$ is selected from the group consisting of $-NRS(=O)R^{14}$, $-(C_{1-9}$alkyl$)R^{14}$, -carbocyclyl$R^{14}R^{15}$, -heterocyclyl$R^{14}R^{15}$, -aryl$R^{14}R^{15}$ or -heteroaryl$R^{14}R^{15}$.

In some embodiments, one of each $R^1$ and $R^2$, $R^2$ and $R^3$, $R^3$ and $R^4$, $R^6$ and $R^7$, $R^7$ and $R^8$ or $R^8$ and $R^9$ are taken together to form a ring which is selected from the group consisting of aryl, heteroaryl,

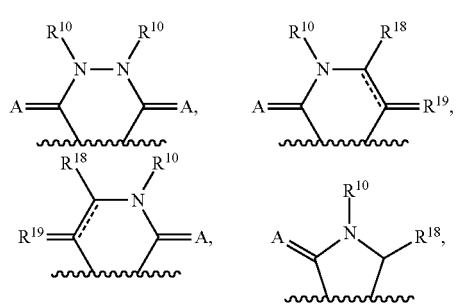

-continued

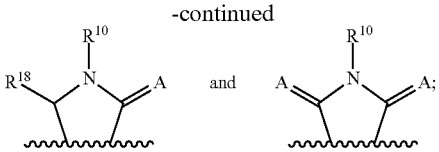

wherein each bond represented by a dashed and solid line represents a bond selected from the group consisting of a single bond and a double bond.

In some embodiments, each $R^{10}$ is independently selected from the group consisting of H, —$C_{1-9}$ alkyl, —$CF_3$, —($C_{1-9}$ alkyl)$_n$carbocyclyl, —($C_{1-9}$ alkyl)$_n$heterocyclyl, —($C_{1-9}$ alkyl)$_n$aryl and —($C_{1-9}$ alkyl)$_n$heteroaryl.

In some embodiments, each $R^{11}$ is independently selected from the group consisting of —$C_{1-9}$ alkyl, —$CF_3$, —($C_{1-9}$ alkyl)$_n$carbocyclyl, —($C_{1-9}$ alkyl)$_n$heterocyclyl, —($C_{1-9}$ alkyl)$_n$aryl and —($C_{1-9}$ alkyl)$_n$heteroaryl.

In some embodiments, each $R^{12}$ is independently selected from the group consisting of —$OR^{10}$ and $R^{10}$.

In some embodiments, each $R^{13}$ is 1-5 substituents each selected from the group consisting of H, $C_{1-9}$ alkyl, halide, —$CF_3$, carbocyclyl$R^{13}$, heterocyclyl$R^{13}$, aryl$R^{13}$, heteroaryl$R^{13}$, —($C_{1-9}$ alkyl)$_n$$OR^{10}$, —($C_{1-9}$ alkyl)$_n$$SR^{10}$, —($C_{1-9}$ alkyl)$_n$S(=O)$R^{11}$, —($C_{1-9}$ alkyl)$_n$$SO_2R^{10}$, —($C_{1-9}$ alkyl)$_n$N($R^{10}$)$SO_2R^{10}$, —($C_{1-9}$ alkyl)$_n$$SO_2N(R^{10})_2$, —($C_{1-9}$ alkyl)$_n$N($R^{10}$)$_2$, —($C_{1-9}$ alkyl)$_n$N($R^{10}$)C(=A)N($R^{10}$)$_2$, —($C_{1-9}$ alkyl)$_n$C(=A)N($R^{10}$)$_2$, —($C_{1-9}$ alkyl)$_n$N($R^{10}$)C(=A)$R^{10}$, —$NO_2$, —CN, —($C_{1-9}$ alkyl)$_n$$CO_2R^{10}$ and —($C_{1-9}$ alkyl)$_n$C(=A)$R^{10}$.

In some embodiments, $R^{14}$ is selected from the group consisting of —$NR^{10}C(=A)R^{10}$, —$NR^{10}S(=O)R^{11}$, —$NR^{10}SO_2R^{10}$, —$NR^{10}C(=O)N(R^{16})_2$, —$NR^{10}C(=S)N(R^{10})_2$, —$NR^{10}C(=NR^{12})N(R^{10})_2$, —$N(R^{16})_2$, —$C(=O)NR^{10}R^{17}$, —$C(=S)N(R^{10})_2$, —$C(=NR^{12})N(R^{10})_2$, —$OC(=A)R^{10}$, —$C(=A)R^{10}$, —$NR^{10}C(=A)OR^{10}$ and —$OC(=A)NR^{10}R^{10}$.

In some embodiments, $R^{15}$ is 1-4 substituents each selected from the group consisting of H, $C_{1-9}$ alkyl, halide, —$CF_3$, carbocyclyl$R^{13}$, heterocyclyl$R^{13}$, aryl$R^{13}$, heteroaryl$R^{13}$, —($C_{1-9}$ alkyl)$_n$$OR^{10}$, —($C_{1-9}$ alkyl)$_n$$SR^{10}$, —($C_{1-9}$ alkyl)$_n$S(=O)$R^{11}$, —($C_{1-9}$ alkyl)$_n$$SO_2R^{10}$, —($C_{1-9}$ alkyl)$_n$N($R^{10}$)$SO_2R^{10}$, —($C_{1-9}$ alkyl)$_n$$SO_2N(R^{10})_2$, —($C_{1-9}$ alkyl)$_n$N($R^{10}$)$_2$, —($C_{1-9}$ alkyl)$_n$N($R^{10}$)C(=A)N($R^{10}$)$_2$, —($C_{1-9}$ alkyl)$_n$C(=A)N($R^{10}$)$_2$, —($C_{1-9}$ alkyl)$_n$N($R^{10}$)C(=A)$R^{10}$, —$NO_2$, —CN, —($C_{1-9}$ alkyl)$_n$$CO_2R^{10}$ and —($C_{1-9}$ alkyl)$_n$C(=A)$R^{10}$.

In some embodiments, $R^{16}$ is —$C_{1-9}$ alkyl.

In some embodiments, each $R^{17}$ is independently selected from the group consisting of -heterocyclyl$R^{13}$, —($C_{1-9}$ alkyl)heterocyclyl$R^{13}$ and —($C_{1-9}$ alkyl)carbocyclyl$R^{13}$.

In some embodiments, $R^{18}$ and $R^{19}$ are independently selected from the group consisting of H, $C_{1-9}$ alkyl, halide, —($C_{1-9}$ alkyl)$_n$carbocyclyl$R^{13}$, —($C_{1-9}$ alkyl)$_n$heterocyclyl$R^{13}$, —($C_{1-9}$ alkyl)$_n$aryl$R^{13}$, —($C_{1-9}$ alkyl)$_n$heteroaryl$R^{13}$, —($C_{1-9}$ alkyl)$_n$$OR^{10}$, —($C_{1-9}$ alkyl)$_n$$SR^{10}$, —($C_{1-9}$ alkyl)$_n$S(=O)$R^{11}$, —($C_{1-9}$ alkyl)$_n$$SO_2R^{10}$, —($C_{1-9}$ alkyl)$_n$N($R^{10}$)$SO_2R^{10}$, —($C_{1-9}$ alkyl)$_n$$SO_2N(R^{10})_2$, —($C_{1-9}$ alkyl)$_n$N($R^{10}$)$_2$, —($C_{1-9}$ alkyl)$_n$N($R^{10}$)C(=A)N($R^{10}$)$_2$, —($C_{1-9}$ alkyl)$_n$C(=A)N($R^{10}$)$_2$, —($C_{1-9}$ alkyl)$_n$N($R^{10}$)C(=A)$R^{10}$, —$NO_2$, —CN, —($C_{1-9}$ alkyl)$_n$$CO_2R^{10}$ and —($C_{1-9}$ alkyl)$_n$C(=A)$R^{10}$.

In some embodiments, $R^{18}$ and $R^{19}$ are taken together to form a ring which is selected from the group consisting of benzene and pyridine.

In some embodiments, each A is independently selected from O, S and $NR^{12}$.

In some embodiments, $Y^1$, $Y^2$, $Y^3$ and $Y^4$ are independently selected from the group consisting of carbon and nitrogen with the proviso that at least one of $Y^1$, $Y^2$, $Y^3$ and $Y^4$ are nitrogen.

In some embodiments, $Y^1$ is nitrogen and $R^6$ is absent.
In some embodiments, $Y^2$ is nitrogen and $R^7$ is absent.
In some embodiments, $Y^3$ is nitrogen and $R^8$ is absent.
In some embodiments, $Y^4$ is nitrogen and $R^9$ is absent.
In some embodiments, each n is 0 or 1.

Some embodiments of the present invention include compounds, salts, pharmaceutically acceptable salts or pro-drug thereof of formula (Ib):

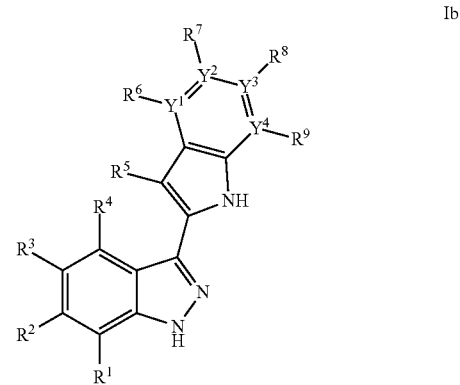

Ib

In some embodiments, $R^1$, $R^2$, $R^3$, $R^4$, $R^5$, $R^6$, $R^7$, $R^8$ and $R^9$ are independently selected from the group consisting of H, $C_{1-9}$ alkyl, halide, —$CF_3$, —($C_{1-9}$ alkyl)$_n$carbocyclyl$R^{13}$, —($C_{1-9}$ alkyl)$_n$heterocyclyl$R^{13}$, —($C_{1-9}$ alkyl)$_n$aryl$R^{13}$, —($C_{1-9}$ alkyl)$_n$heteroaryl$R^{13}$, —($C_{1-9}$ alkyl)$_n$$OR^{10}$, —($C_{1-9}$ alkyl)$_n$$SR^{10}$, —($C_{1-9}$ alkyl)$_n$S(=O)$R^{11}$, —($C_{1-9}$ alkyl)$_n$$SO_2R^{10}$, —($C_{1-9}$ alkyl)$_n$N($R^{10}$)$SO_2R^{10}$, —($C_{1-9}$ alkyl)$_n$$SO_2N(R^{10})_2$, —($C_{1-9}$ alkyl)$_n$N($R^{10}$)$_2$, —($C_{1-9}$ alkyl)$_n$N($R^{10}$)C(=A)N($R^{10}$)$_2$, —($C_{1-9}$ alkyl)$_n$C(=A)N($R^{10}$)$_2$, —($C_{1-9}$ alkyl)$_n$N($R^{10}$)C(=A)$R^{10}$, —$NO_2$, —CN, —($C_{1-9}$ alkyl)$_n$$CO_2R^{10}$ and —($C_{1-9}$ alkyl)$_n$C(=A)$R^{10}$.

In some embodiments, one of each $R^1$ and $R^2$, $R^2$ and $R^3$, $R^3$ and $R^4$, $R^6$ and $R^7$, $R^7$ and $R^8$ or $R^8$ and $R^9$ are taken together to form a ring which is selected from the group consisting of aryl, heteroaryl,

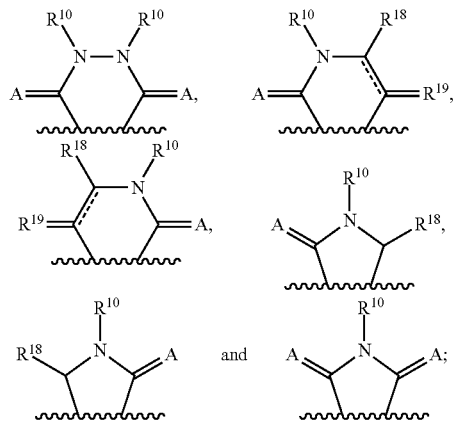

wherein each bond represented by a dashed and solid line represents a bond selected from the group consisting of a single bond and a double bond.

In some embodiments, each $R^{10}$ is independently selected from the group consisting of H, —$C_{1-9}$ alkyl, —$CF_3$, —($C_{1-9}$ alkyl)$_n$carbocyclyl, —($C_{1-9}$ alkyl)$_n$heterocyclyl, —($C_{1-9}$ alkyl)$_n$aryl and —($C_{1-9}$ alkyl)$_n$heteroaryl.

In some embodiments, each $R^{11}$ is independently selected from the group consisting of —$C_{1-9}$ alkyl, —$CF_3$, —($C_{1-9}$ alkyl)$_n$carbocyclyl, —($C_{1-9}$ alkyl)$_n$heterocyclyl, —($C_{1-9}$ alkyl)$_n$aryl and —($C_{1-9}$ alkyl)$_n$heteroaryl.

In some embodiments, each $R^{12}$ is independently selected from the group consisting of —$OR^{10}$ and $R^{10}$.

In some embodiments, each $R^{13}$ is 1-5 substituents each selected from the group consisting of H, $C_{1-9}$ alkyl, halide, —$CF_3$, carbocyclyl$R^{13}$, heterocyclyl$R^{13}$, aryl$R^{13}$, heteroaryl$R^{13}$, —($C_{1-9}$ alkyl)$_n$$OR^{10}$, —($C_{1-9}$ alkyl)$_n$$SR^{10}$, —($C_{1-9}$ alkyl)$_n$S(=O)$R^{11}$, —($C_{1-9}$ alkyl)$_n$$SO_2R^{10}$, —($C_{1-9}$ alkyl)$_n$N($R^{10}$)$SO_2R^{10}$, —($C_{1-9}$ alkyl)$_n$$SO_2$N($R^{10}$)$_2$, —($C_{1-9}$ alkyl)$_n$N($R^{10}$)$_2$, —($C_{1-9}$ alkyl)$_n$N($R^{10}$)C(=A)N($R^{10}$)$_2$, —($C_{1-9}$ alkyl)$_n$C(=A)N($R^{10}$)$_2$, —($C_{1-9}$ alkyl)$_n$N($R^{10}$)C(=A)$R^{10}$, —$NO_2$, —CN, —($C_{1-9}$ alkyl)$_n$$CO_2R^{10}$ and —($C_{1-9}$ alkyl)$_n$C(=A)$R^{10}$.

In some embodiments, $R^{18}$ and $R^{19}$ are independently selected from the group consisting of H, $C_{1-9}$ alkyl, halide, —($C_{1-9}$ alkyl)$_n$carbocyclyl$R^{13}$, —($C_{1-9}$ alkyl)$_n$heterocyclyl$R^{13}$, —($C_{1-9}$ alkyl)$_n$aryl$R^{13}$, —($C_{1-9}$ alkyl)$_n$heteroaryl$R^{13}$, —($C_{1-9}$ alkyl)$_n$$OR^{10}$, —($C_{1-9}$ alkyl)$_n$$SR^{10}$, —($C_{1-9}$ alkyl)$_n$S(=O)$R^{11}$, —($C_{1-9}$ alkyl)$_n$$SO_2R^{10}$, —($C_{1-9}$ alkyl)$_n$N($R^{10}$)$SO_2R^{10}$, —($C_{1-9}$ alkyl)$_n$$SO_2$N($R^{10}$)$_2$, —($C_{1-9}$ alkyl)$_n$N($R^{10}$)$_2$, —($C_{1-9}$ alkyl)$_n$N($R^{10}$)C(=A)N($R^{10}$)$_2$, —($C_{1-9}$ alkyl)$_n$C(=A)N($R^{10}$)$_2$, —($C_{1-9}$ alkyl)$_n$N($R^{10}$)C(=A)$R^{10}$, —$NO_2$, —CN, —($C_{1-9}$ alkyl)$_n$$CO_2R^{10}$ and —($C_{1-9}$ alkyl)$_n$C(=A)$R^{10}$.

In some embodiments, $R^{18}$ and $R^{19}$ are taken together to form a ring which is selected from the group consisting of benzene and pyridine.

In some embodiments, each A is independently selected from O, S and $NR^{12}$.

In some embodiments, $Y^1$, $Y^2$, $Y^3$ and $Y^4$ are independently selected from the group consisting of carbon and nitrogen with the proviso that at least one of $Y^1$, $Y^2$, $Y^3$ and $Y^4$ are nitrogen.

In some embodiments, $Y^1$ is nitrogen and $R^6$ is absent.
In some embodiments, $Y^2$ is nitrogen and $R^7$ is absent.
In some embodiments, $Y^3$ is nitrogen and $R^8$ is absent.
In some embodiments, $Y^4$ is nitrogen and $R^9$ is absent.
In some embodiments, each n is 0 or 1.

Illustrative compounds of Formula (Ia) and (Ib) are shown in Table 1.

TABLE 1

| # | Structure |
|---|---|
| 1 | (piperidin-4-yl)amide of pyridine-nicotinamide linked to 3-(1H-imidazo[4,5-b]pyridin-2-yl)-1H-indazole |
| 2 | (cyclohexylmethyl)amide of pyridine-nicotinamide linked to 3-(1H-imidazo[4,5-c]pyridin-2-yl)-1H-indazole |
| 3 | (cyclopropylmethyl)amide of pyridine-nicotinamide linked to 3-(1H-imidazo[4,5-c]pyridin-2-yl)-1H-indazole |
| 4 | propanamide of aminopyridine linked to 3-(1H-imidazo[4,5-c]pyridin-2-yl)-1H-indazole |
| 5 | N,N-dimethylurea of aminopyridine linked to 3-(1H-imidazo[4,5-c]pyridin-2-yl)-1H-indazole |
| 6 | methyl carbamate of aminopyridine linked to 3-(1H-imidazo[4,5-c]pyridin-2-yl)-1H-indazole |

TABLE 1-continued
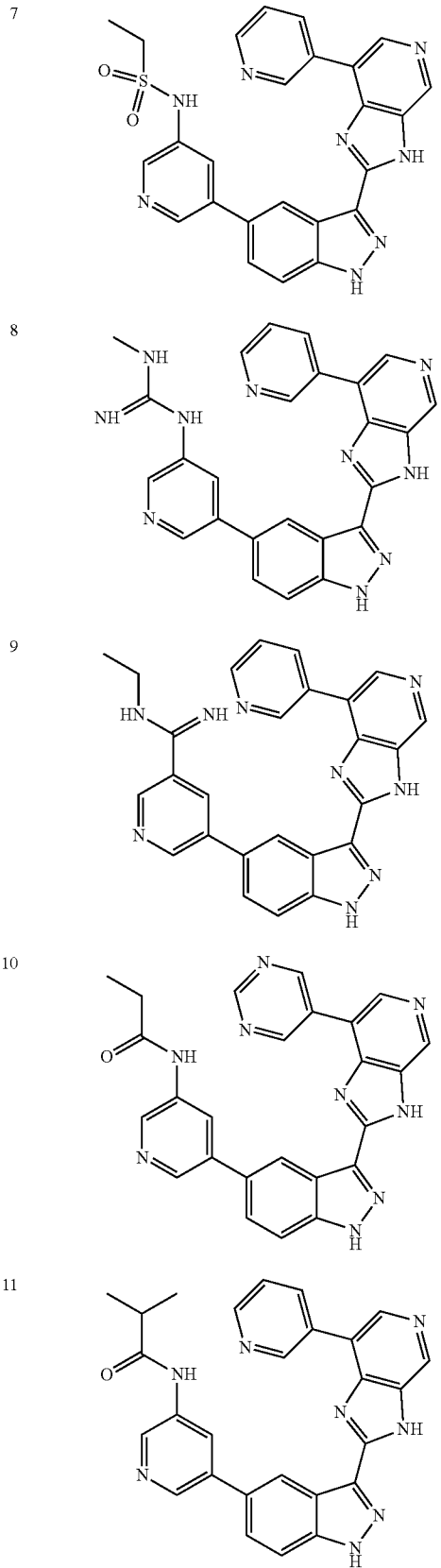
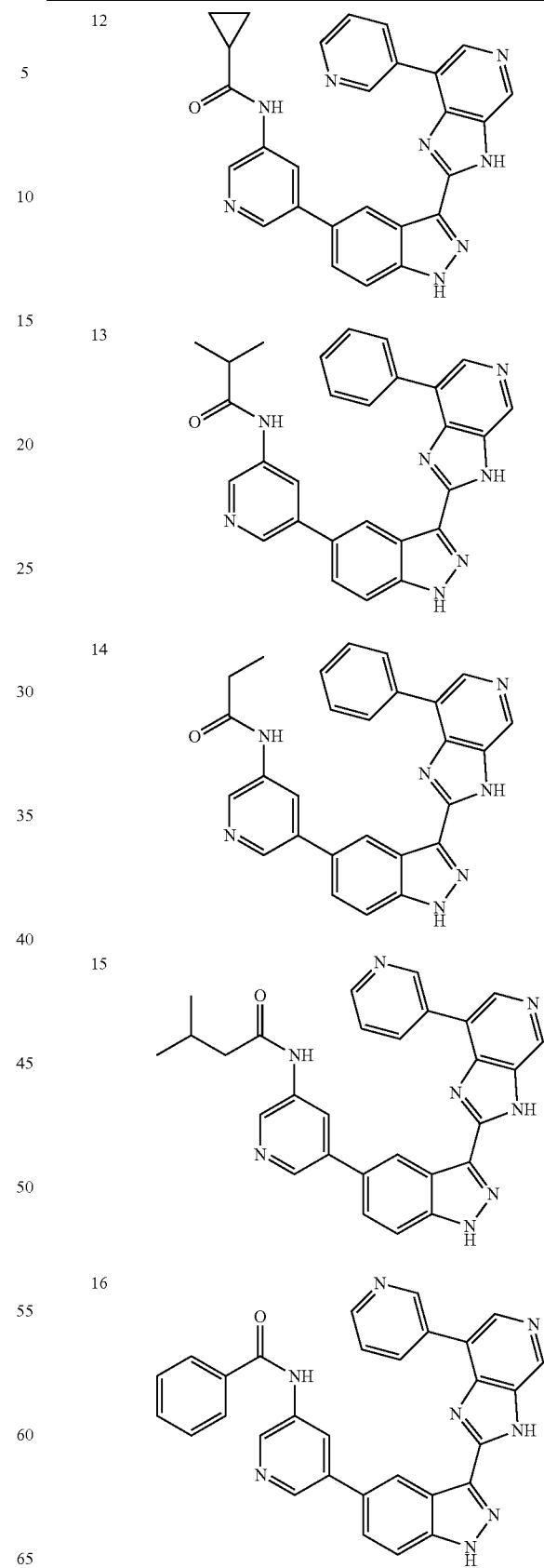

TABLE 1-continued

| 17 | 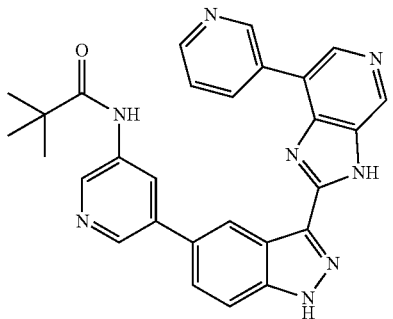 |
| --- | --- |
| 18 | 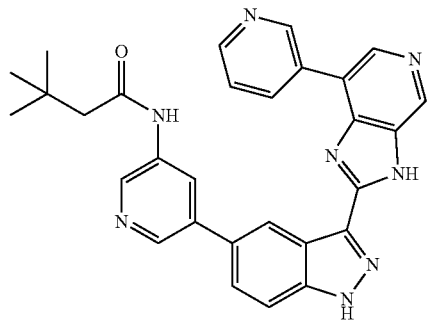 |
| 19 | 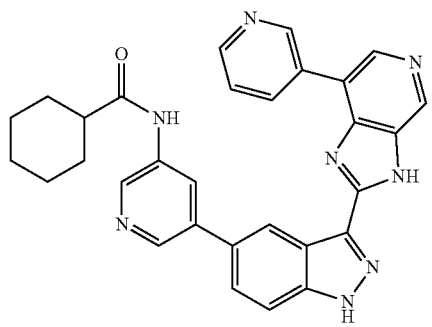 |
| 20 | 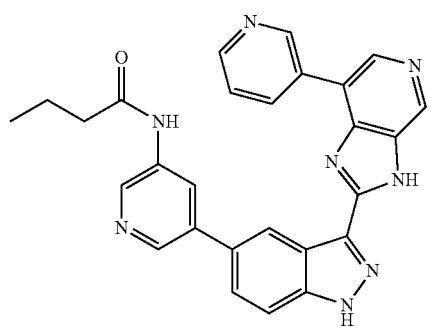 |
| 21 | 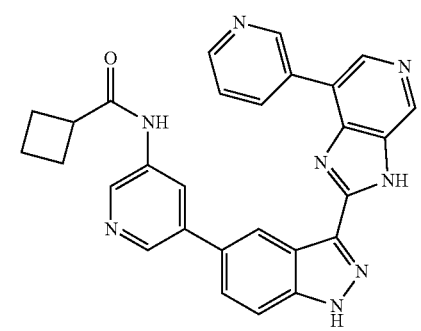 |

TABLE 1-continued

| 22 | 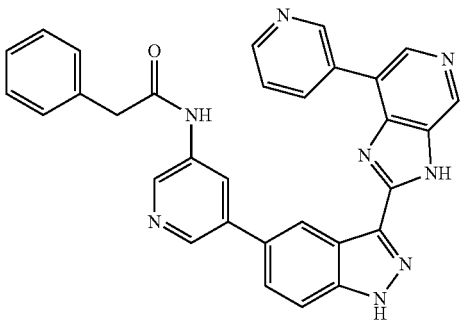 |
| --- | --- |
| 23 | 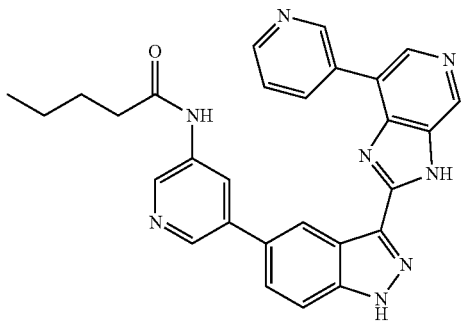 |
| 24 | 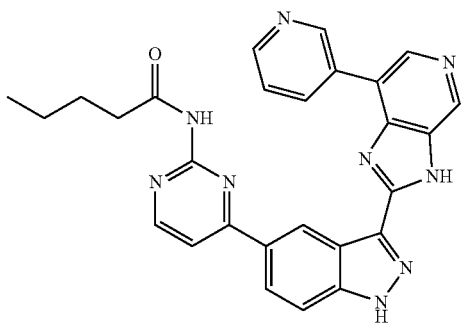 |

Compound Preparation

The starting materials used in preparing the compounds of the invention are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as *March's Advanced Organic Chemistry: Reactions, Mechanisms, and Structure* 6$^{th}$ Ed., John Wiley & Sons (2007), Carey and Sundberg, *Advanced Organic Chemistry* 5$^{th}$ Ed., Springer (2007), *Comprehensive Organic Transformations: A Guide to Functional Group Transformations*, 2$^{nd}$ Ed., John Wiley & Sons (1999) (incorporated herein by reference in its entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts *Protecting Groups in Organic Synthesis,* 4th Ed., John Wiley & Sons (2007), incorporated herein by reference in its entirety.

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

$^1$H nuclear magnetic resonance spectra (NMR) were measured in the indicated solvents on a Bruker NMR spectrometer (Avance™ DRX300, 300 MHz for 1H). Peak positions are expressed in parts per million (ppm) downfield from tetramethylsilane. The peak multiplicities are denoted as follows, s, singlet; d, doublet; t, triplet; m, multiplet.

The following abbreviations have the indicated meanings:
brine=saturated aqueous sodium chloride
CDCl$_3$=deuterated chloroform
DCM=dichloromethane
DHP=3,4-dihydro-2H-pyran
DMF=N,N-dimethylformamide
DMSO-d$_6$=deuterated dimethylsulfoxide
ESIMS=electron spray mass spectrometry
EtOAc=ethyl acetate
Et$_3$SiH=triethylsilane
HCl=hydrochloric acid
HOAc=acetic acid
KOH=potassium hydroxide
K$_3$PO$_4$=potassium phosphate
LAH=lithium aluminum hydride
MeOH=methanol
MgSO$_4$=magnesium sulfate
Na$_2$CO$_3$=sodium carbonate
NaHCO$_3$=sodium bicarbonate
NaHSO$_3$=sodium bisulfite
NaOAc=sodium acetate
NMR=nuclear magnetic resonance
Pd/C=palladium on carbon
PdCl$_2$(dppf)$_2$=1,1'-bis(diphenylphosphino)ferrocene-palladium(II)dichloride
Pd(PPh$_3$)$_2$Cl$_2$=dichloro-bis(triphenylphosphine)palladium (II)
Pd(PPh$_3$)$_4$=tetrakis(triphenylphosphine)palladium(0)
PPTS=pyridinium p-toluenesulfonate
rt=room temperature
TFA=trifluoroacetic acid
THF=tetrahydrofuran
TLC=thin layer chromatography The following example schemes are provided for the guidance of the reader, and collectively represent an example method for making the compounds provided herein. Furthermore, other methods for preparing compounds of the invention will be readily apparent to the person of ordinary skill in the art in light of the following reaction schemes and examples. Unless otherwise indicated, all variables are as defined above.

General Procedures

Compounds of Formula Ia of the present invention can be prepared as depicted in Scheme 1.

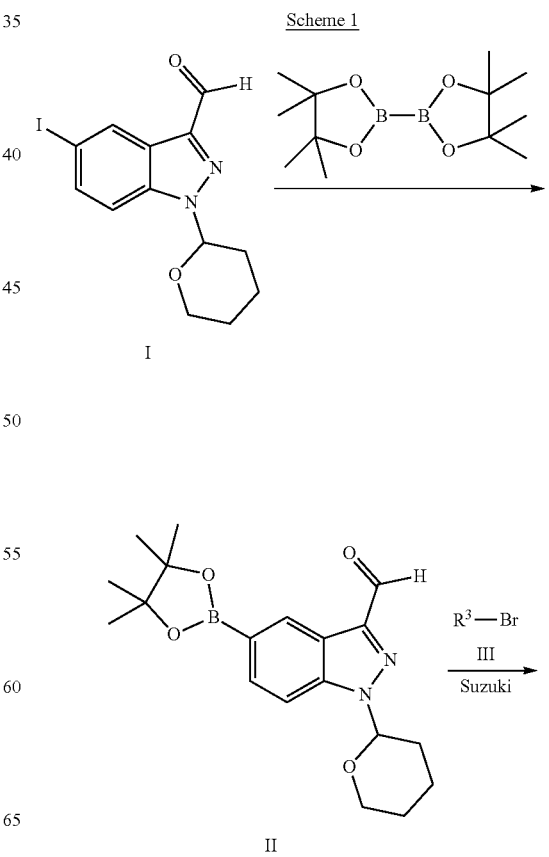

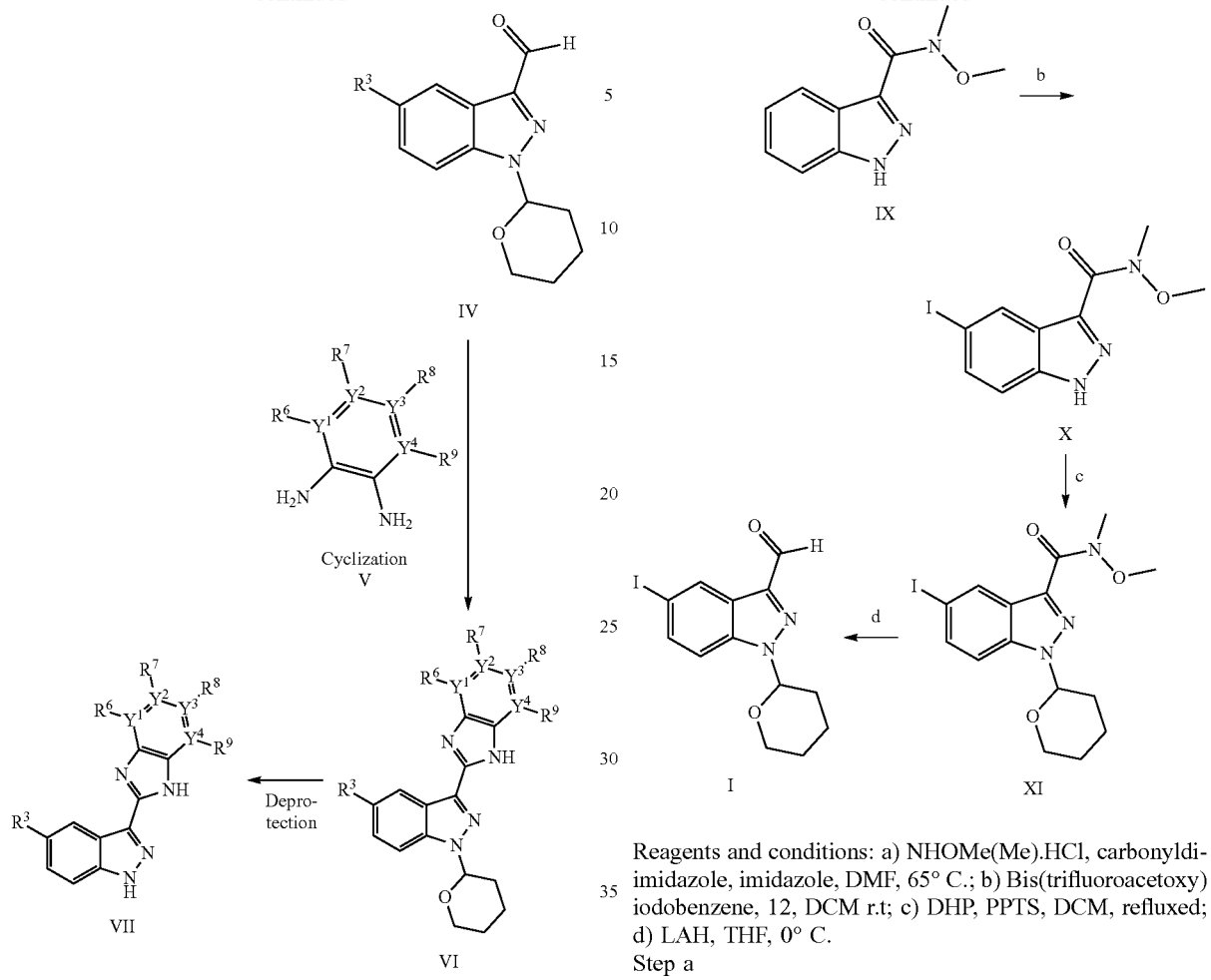

Scheme 1 describes a method for preparation of indazole derivatives (VII) by first reacting 5-iodo-1-(tetrahydro-2H-pyran-2-yl)-1H-indazole-3-carbaldehyde (I) with bis(pinacolato)diboron to form the borate ester (II). Suzuki coupling with various bromides (III) yields indazole derivatives (IV). Aldehyde (IV) is reacted with various 1,2-diamines (V) to produce (VI). Final deprotection of the pyrazole nitrogen yields the desired indazole derivatives (VII).

ILLUSTRATIVE COMPOUND EXAMPLES

Preparation of intermediate (I) is depicted below in Scheme 2.

Scheme 2

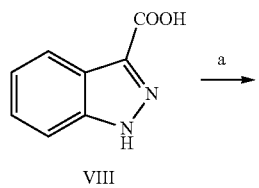

VIII

Reagents and conditions: a) NHOMe(Me).HCl, carbonyldiimidazole, imidazole, DMF, 65° C.; b) Bis(trifluoroacetoxy)iodobenzene, 12, DCM r.t; c) DHP, PPTS, DCM, refluxed; d) LAH, THF, 0° C.

Step a 1H-indazole-3-carboxylic acid (VIII) (100 g, 617 mmol) in DMF was treated with carbonyldiimidazole (110 g, 678 mmol) at r.t. until the evolution of gas ceased (ca. 15 minutes). The reaction was heated to 60-65° C. for two hours and then allowed to cool to r.t. N,O-Dimethylhydroxylamine-HCl (66.2 g, 678 mmol) was added as a solid and the mixture was heated to 65° C. for 3 hours. The reaction was concentrated to a paste and taken up in DCM, and washed subsequently with water and 2N HCl. The product could be seen coming out of solution. The solid was filtered and rinsed separately with EtOAc. The EtOAc and DCM layers were separately washed with sodium bicarbonate followed by brine, dried over $MgSO_4$ and concentrated under reduced pressure. The resulting solids were combined, triturated with 1:1 mixture of DCM-ether, filtered, and dried to produce N-methoxy-N-methyl-1H-indazole-3-carboxamide (IX) as a white solid (100 g, 487 mmol, 79% yield). $^1$H NMR (DMSO-$d_6$) δ ppm 3.46 (s, 3H), 3.69-3.85 (m, 3H), 7.13-7.31 (m, 1H), 7.41 (t, J=7.25 Hz, 1H), 7.56-7.65 (m, 1H), 7.93-8.08 (m, 1H); ESIMS found for $C_{10}H_{11}N_3O_2$ m/z 206 (M+H).

Step b

To the N-methoxy-N-methyl-1H-indazole-3-carboxamide (IX) (20 g, 97.4 mmol) in 1 L DCM was added bis(trifluoroacetoxy)iodobenzene (46 g, 107 mmol) followed by portionwise addition of iodine (14.84 g, 58.5 mmol) at r.t. After 1 hour, 600 mL of saturated $NaHSO_3$ was added and a solid began to precipitate which was filtered and rinsed with excess DCM. The filtrate was washed with brine, dried over MgSO₄, concentrated and the remaining solid was triturated with a minimal amount of DCM. The combined solids were dried under vacuum over KOH to produce 5-iodo-N-methoxy-N-methyl-1H-indazole-3-carboxamide (X) as a white solid (23.2 g, 70 mmol, 72% yield). ¹H NMR (DMSO-d₆) δ ppm 3.45 (s, 4H), 3.77 (s, 4H), 7.45-7.54 (m, 1H), 7.66 (dd, J=8.81, 1.51 Hz, 1H), 8.40 (d, J=1.01 Hz, 1H); ESIMS found for $C_{10}H_{10}N_3O_2$ m/z 331 (M+H).

Step c

A mixture of 5-iodo-N-methoxy-N-methyl-1H-indazole-3-carboxamide (X) (16.5 g, 50 mmol), 3,4-dihydro-2H-pyran (10.3 mL, 113 mmol) and PPTS (0.12 g, 0.6 mmol) in DCM was heated to reflux for 5 hours. The solution was poured into a saturated NaHCO₃ solution, the layers were separated, and the aqueous layer was extracted with DCM. The combined organic layers were washed with 5% aqueous citric acid and brine, dried over MgSO₄, and concentrated. The crude product was purified on a silica gel column (100% EtOAc→3:97 MeOH:DCM) to provide 5-iodo-N-methoxy-N-methyl-1-(tetrahydro-2H-pyran-2-yl)-1H-indazole-3-carboxamide (XI) as a white viscous oil (19.1 g, 46 mmol, 92% yield). ¹H NMR (DMSO-d₆) δ ppm 1.28-1.84 (m, 6H), 3.43 (s, 3H), 3.60-4.04 (s, 5H), 5.86-6.08 (m, 1H), 7.45-7.87 (m, 2H), 8.39 (s, 1H); ESIMS found for $C_{15}H_{18}IN_3O_3$ m/z 416 (M+H).

Step d

Lithium aluminum hydride (160 mg, 4.21 mmol) was added in portions to a cooled (0° C.) solution of 5-iodo-N-methoxy-N-methyl-1-(tetrahydro-2H-pyran-2-yl)-1H-indazole-3-carboxamide (XI) (1.46 g, 3.5 mmol) in THF. Stirring was continued at 0° C. until the reaction was completed, approximately 30 min. The reaction was quenched by the slow addition of EtOAc at 0° C., and the whole mixture was poured into 0.4 N NaHSO₄. The organic layer was washed with brine, dried over MgSO₄, concentrated, and purified on a silica gel column (100% EtOAc→3:97 MeOH:DCM) to give 5-iodo-1-(tetrahydro-2H-pyran-2-yl)-1H-indazole-3-carbaldehyde (I) as a white solid (0.90 g, 3.15 mmol, 72% yield). ¹H NMR (DMSO-d₆) δ ppm 1.50-1.71 (m, 2H), 1.71-1.87 (m, 1H), 1.97-2.15 (m, 2H), 2.31-2.42 (m, 1H), 3.66-3.99 (m, 2H), 5.96-6.17 (m, 1H), 7.78 (d, J=6 Hz, 1H), 7.84 (d, J=6 Hz, 1H), 8.50 (s, 1H), 10.13 (s, 1H); ESIMS found for $C_{13}H_{13}IN_2O_2$ m/z 357 (M+H).

Preparation of intermediate (XV) is depicted below in Scheme 3.

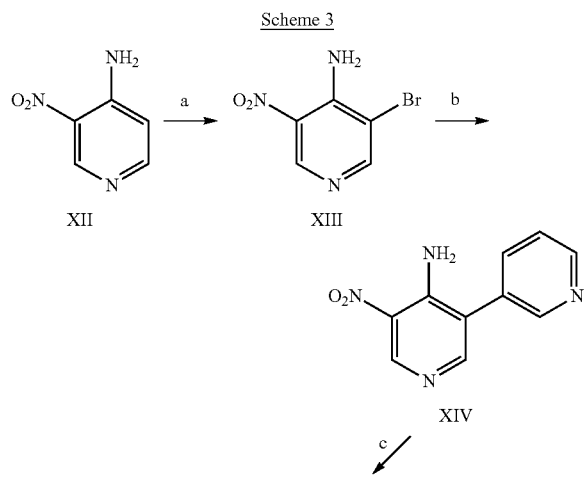

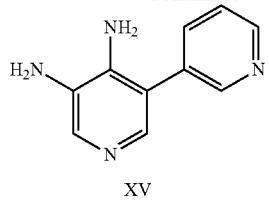

Reagents and conditions: a) HOAc, NaOAc, Br₂, 100° C., 28 h, b) 1,4-Dioxane, pyridyl-3-boronic acid, Na₂CO₃, H₂O, Pd(PPh₃)₂Cl₂, reflux., 15 h, c) MeOH, Pd/C, H₂, rt, 15 h Step a A mixture of 3-nitropyridin-4-amine (XII) (10 g, 71.94 mmol) and acetic acid (120 ml) was added to a sealed tube followed by addition of NaOAc (29.50 g, 93.52 mmol) and dropwise addition of bromine (4.7 ml 359.7 mmol) under stirring. The sealed tube was heated at 100° C. for 28 h until TLC showed consumption of starting material. The reaction mixture was concentrated to obtain a solid which was dissolved in water, basified with NaHCO₃ and extracted with ethyl acetate. The combined organic extracts were dried and concentrated to produce 3-bromo-5-nitropyridin-4-amine (XIII) as a yellow solid (12 g, 55 mmol, 77% yield). ¹H NMR (DMSO-d₆) δ ppm 9.19 (s, 1H), 8.58 (s, 1H); ESIMS found for $C_5H_4BrN_3O_2$ m/z 217, 219 (M+, M+2).

Step b

A solution of 3-bromo-5-nitropyridin-4-amine (XIII) (6 g, 26 mmol), pyridin-3-ylboronic acid (3.54 g, 29 mmol), 1 N Na₂CO₃ solution (78 ml) and 1,4-dioxane (150 mL) was degassed with argon thrice. Pd(PPh₃)₂Cl₂ (927 mg, 5 mmol %) was added to the reaction and the solution was refluxed for 15 h until TLC showed the reaction was complete. The reaction was passed through a pad of Celite and then concentrated under reduced pressure. The reaction mixture was concentrated and the residue was taken up in ethyl acetate. The organic extract was washed with water, dried and concentrated under vacuum. The crude product was purified on a silica gel column (100% EtOAc→2:98 MeOH:DCM) to give 5-nitro-3,3'-bipyridin-4-amine (XIV) as a yellow solid (5 g, 23.1 mmol, 87% yield). ¹H NMR (CDCl₃, 400 MHz) δ ppm 9.31 (s, 1H), 8.80-8.79 (m, 1H), 8.70 (s, 1H), 8.23 (s, 1H), 7.80-7.73 (m, 1H), 7.52-7.48 (m, 1H). ESIMS found $C_{10}H_8N_4O_2$ m/z 216.95 (M+H).

Step c

To a solution of 5-nitro-3,3'-bipyridin-4-amine (XIV) (5 g, 23 mmol) in MeOH (20 mL) was added 10% Pd/C. The solution was purged with hydrogen and stirred at r.t. under hydrogen for 15 h. The suspension was filtered through Celite and the concentrated under vacuum to produce 3,3'-bipyridine-4,5-diamine (XV) as off white solid (3.3 g, 17.7 mmol, 76% yield). ¹H NMR (DMSO-d₆, 400 MHz): δ 8.63-8.53 (m, 1H), 7.90-7.83 (m, 1H), 7.75 (s, 1H), 7.58 (s, 1H), 7.48-7.43 (m, 2H), 6.13 (bs, 2H), 5.31 (bs, 2H). ESIMS found $C_{10}H_{10}N_4$ m/z 187.10 (M+H).

Preparation of intermediate (XVII) is depicted below in Scheme 4.

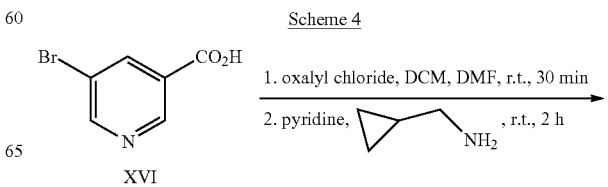

XVII (structure: 5-bromo-N-(cyclopropylmethyl)nicotinamide)

Step 1-2

To a solution of 5-bromonicotinic acid (XVI) (1.01 g, 5 mmol) in dry DCM (10 mL) under nitrogen was added oxalyl chloride (0.654 mL, 7.5 mmol) followed by dry DMF (0.1 mL). The solution was stirred at r.t. for 30 min. The solvent was evaporated under vacuum before adding dry pyridine (10 mL) followed by cyclopropylmethanamine (0.39 mL, 4.5 mmol). The solution was stirred at r.t. under nitrogen for 2 h. The solution was poured into ice water, basified with sat. aq. NaHCO$_3$ and extracted with DCM. The combined organic phases were dried over MgSO$_4$, concentrated and dried under vacuum to yield 5-bromo-N-(cyclopropylmethyl) nicotinamide (XVII) as an off-white solid (0.82 g, 3.2 mmol, 71% yield). $^1$H NMR (DMSO-d$_6$) δ ppm −0.07-0.07 (m, 2H), 0.15-0.29 (m, 2H), 0.68-0.88 (m, 1H), 2.93 (t, J=6.22 Hz, 2H), 8.20 (t, J=1.88 Hz, 1H), 8.62 (d, J=1.70 Hz, 2H), 8.75 (s, 1H); ESIMS found C$_{10}$H$_{11}$BrN$_2$O m/z 254, 256 (M+, M+2).

Preparation of intermediate (XX) is depicted below in Scheme 5.

Scheme 5

XVIII + XIX → (Pyridine, 0° C.-r.t., 15 h) → XX

Step 1

3-Amino-5-bromo pyridine (XVIII) (1 eq) was dissolved in DCM and cooled to 0° C. before adding pyridine (2.2 eq) and isobutyryl chloride (XIX) (1.1 eq). The reaction mixture was stirred at r.t. for 15 h until TLC showed the reaction was complete. The reaction mixture was diluted with DCM and washed with water. The organic extract was dried, concentrated and purified by column chromatography using silica gel (100-200 mesh) to afford N-(5-bromopyridin-3-yl)isobutyramide (XX) as a off white solid, (71% yield). $^1$H NMR (CDCl$_3$) δ ppm 8.55-8.35 (m, 3H), 7.32 (s, 1H), 2.59-2.48 (m, 1H), 1.28-1.27 (d, 6H); ESIMS found C$_9$H$_{11}$BrN$_2$O m/z 243.05 (M+H).

The following intermediates were prepared in accordance with the procedure described in the above Scheme 5.

XXI

N-(5-bromopyridin-3-yl)pivalamide (XXI): Off white solid, (67%, yield), $^1$H NMR (CDCl$_3$, 400 MHz) δ ppm 8.48-8.39 (m, 3H), 7.48 (bs, 1H), 1.32 (s, 9H); ESIMS found C$_{10}$H$_{13}$BrN$_2$O m/z 256.80 (M+H).

XXII

N-(5-bromopyridin-3-yl)-3-methylbutanamide (XXII): Off white solid, (67% yield), $^1$H NMR (CDCl$_3$, 400 MHz) δ ppm 8.55-8.42 (m, 3H), 7.62 (s, 1H), 2.31-2.18 (m, 3H), 1.02-1.01 (d, J=6 Hz, 6H); ESIMS found C$_{10}$H$_{13}$BrN$_2$O m/z 258.80 (M+H).

XXIII

N-(5-bromopyridin-3-yl)-3,3-dimethylbutanamide (XXIII): Light yellow solid, (64%, yield), $^1$H NMR (CDCl$_3$, 400 MHz) δ ppm 8.48 (s, 1H), 8.40 (s, 1H), 7.62 (s, 1H), 7.20 (bs, 1H), 2.26 (s, 3H), 1.10 (s, 9H); ESIMS found C$_{11}$H$_{15}$BrN$_2$O m/z 272.80 (M+H).

XXIV

N-(5-bromopyridin-3-yl)butyramide (XXIV): Yellow solid, (86%, yield), $^1$H NMR (CDCl$_3$, 400 MHz) δ ppm 8.48-8.39 (m, 3H), 7.38 (bs, 1H), 2.40-2.36 (t, J=7.2 Hz, 2H), 1.81-1.72 (m, 2H), 1.03-0.98 (t, J=7.2 Hz, 3H); ESIMS found C$_9$H$_{11}$BrN$_2$O m/z 242.90 (M+H).

XXV

N-(5-bromopyridin-3-yl)pentanamide (XXV): Off white solid, (75%, yield), $^1$H NMR (CDCl$_3$, 400 MHz) δ ppm 8.47-8.39 (m, 3H), 7.33 (bs, 1H), 2.41-2.38 (t, 2H, J=7.6 Hz, 2H), 1.75-1.68 (m, 2H), 1.45-1.36 (m, 2H), 0.97-0.93 (t, J=7.2 Hz, 3H); ESIMS found C$_{10}$H$_{13}$BrN$_2$O m/z 256.90 (M+H).

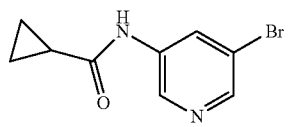

XXVI

N-(5-bromopyridin-3-yl)cyclopropanecarboxamide (XXVI): Off white solid, (83% yield), $^1$H NMR (CDCl$_3$, 400 MHz) δ ppm 8.46-8.39 (m, 3H), 7.54 (bs, 1H), 1.56-1.50 (m, 1H), 1.13-1.07 (m, 2H), 0.96-0.90 (m, 2H); ESIMS found C$_9$H$_9$BrN$_2$O m/z 240.85 (M+H).

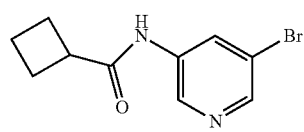

XXVII

N-(5-bromopyridin-3-yl)cyclobutanecarboxamide (XXVII): Off white solid, (54% yield), $^1$H NMR (CDCl$_3$, 400 MHz) δ ppm 8.97-8.39 (m, 3H), 7.21 (bs, 1H), 3.20-3.16 (m, 1H), 2.42-2.24 (m, 4H), 2.05-1.94 (m, 2H); ESIMS found C$_{10}$H$_{11}$BrN$_2$O m/z 256.90 (M+H).

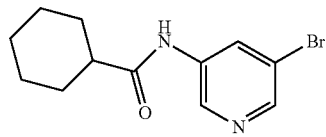

XXVIII

N-(5-bromopyridin-3-yl)cyclohexanecarboxamide (XXVIII): light yellow solid, (89% yield), $^1$H NMR (CDCl$_3$, 400 MHz) δ ppm 8.49-8.38 (m, 3H), 7.61 (bs, 1H), 2.30-2.23 (dd, 1H, J=3.2 Hz, J=11.6 Hz, 1H), 1.96-1.49 (m, 4H), 1.34-1.19 (m, 3H); ESIMS found C$_{12}$H$_{15}$BrN$_2$O m/z 284.75 (M+H).

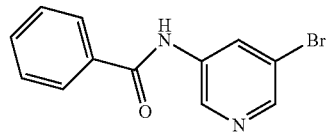

XXIX

N-(5-bromopyridin-3-yl)benzamide (XXIX): Off white solid, (85%, yield), $^1$H NMR (CDCl$_3$, 400 MHz) δ ppm 8.58-8.57 (m, 2H), 8.44-4.43 (d, J=1.6 Hz, 1H), 8.03 (bs, 1H), 7.88-7.86 (d, J=7.2 Hz, 2H), 7.61-7.49 (m, 3H). ESIMS found Cl$_2$H$_9$BrN$_2$O m/z 278.75 (M+H).

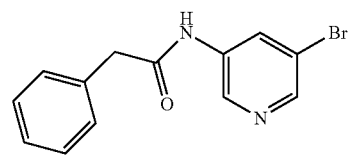

XXX

N-(5-bromopyridin-3-yl)-2-phenylacetamide (XXX): Off white solid, (59%, yield), $^1$H NMR (CDCl$_3$, 400 MHz) δ ppm 8.37-8.31 (m, 3H), 7.41-7.30 (m, 6H), 3.75 (s, 2H); ESIMS found C$_{13}$H$_{11}$BrN$_2$O m/z 292.72 (M+H).

Example 1

Preparation of compound (3) is depicted below in Scheme 6.

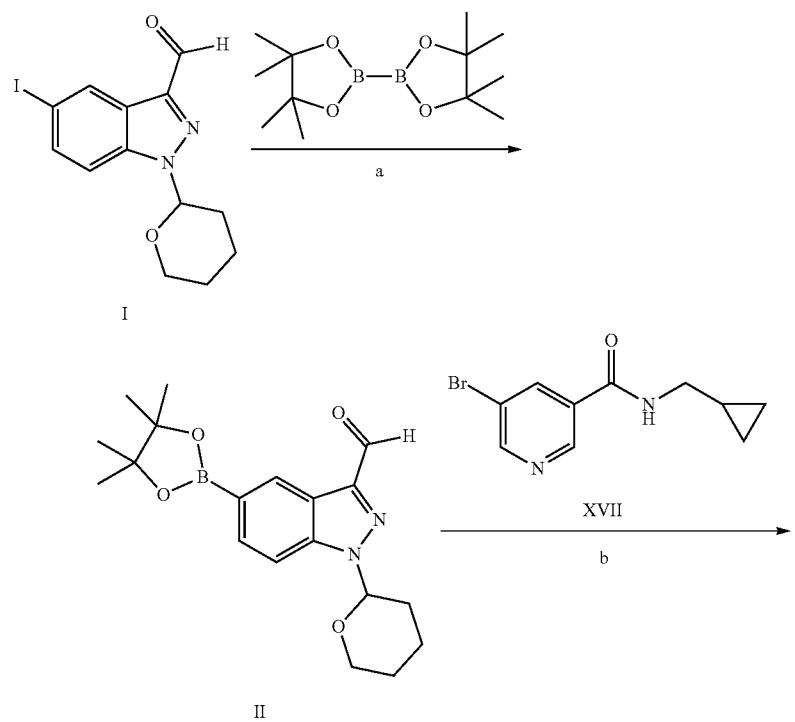

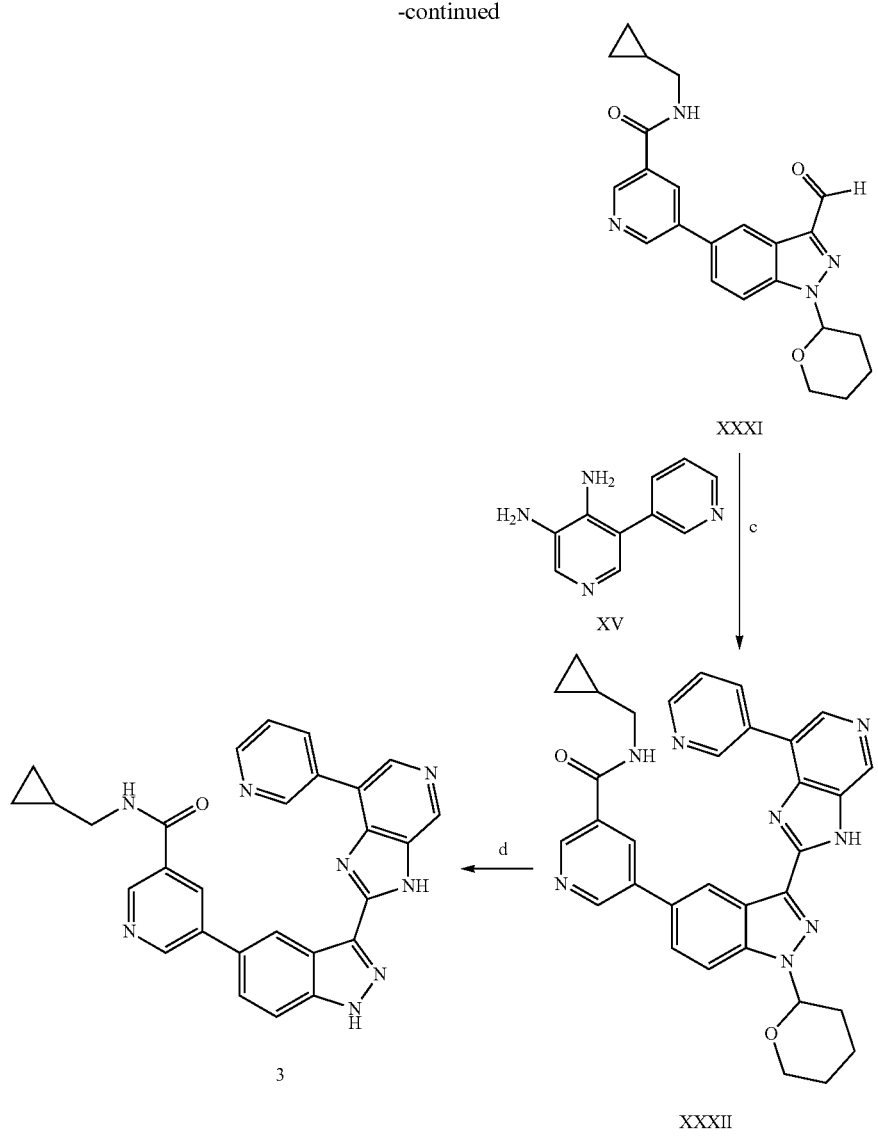

Reagents and conditions: a) KOAc, PdCl$_2$(dppf)$_2$, DMF, 80° C., 2 h; b) K$_2$PO$_4$, Pd(PPh$_3$)$_4$, DMF, H$_2$O, 90° C., 3 h; c) DMF, sulfur, 140° C., ON; d) Et$_3$SiH, DCM, TFA, r.t., 2 h.

Step a-b

A solution of 5-iodo-1-(tetrahydro-2H-pyran-2-yl)-1H-indazole-3-carbaldehyde (I) (1.068 g, 3.0 mmol), bis(pinacolato)diboron (0.914 g, 3.6 mmol), KOAc (0.883 g, 9.0 mmol) and dry DMF (20 mL) was purged with nitrogen. PdCl$_2$(dppf)$_2$ was added to the reaction and purged again with nitrogen. The solution was heated at 80° C. for 2 h. Once TLC showed the disappearance of (I), the solution was cooled to r.t. To this solution was added K$_3$PO$_4$ (0.955 g, 4.5 mmol), 5-bromo-N-(cyclopropylmethyl) nicotinamide (XVII) (0.765 g, 3.0 mmol), Pd(PPh$_3$)$_4$ (104 mg, 0.09 mmol) and water (2 mL). The solution was purged with nitrogen and heated at 90° C. for 3 h. The reaction was passed through a pad of Celite and then concentrated under reduced pressure. The residue was dissolved in DCM and washed with water and brine, dried over MgSO$_4$ and then evaporated under vacuum. The crude product was purified on a silica gel column (100% EtOAc→2:98 MeOH:DCM) to give N-(cyclopropylmethyl)-5-(3-formyl-1-(tetrahydro-2H-pyran-2-yl)-1H-indazol-5-yl)nicotinamide (XXXI) as a yellow solid (1.09 g, 2.7 mmol, 90% yield). $^1$H NMR (DMSO-d$_6$) δ ppm 0.20-0.31 (m, 2H), 0.35-0.57 (m, 2H), 1.65 (m, 2H), 1.74-1.87 (m, 1H), 2.10 (d, J=12.06 Hz, 2H), 2.35-2.44 (m, 1H), 3.10-3.27 (m, 3H), 3.78-3.99 (m, 2H), 6.14 (d, J=7.35 Hz, 1H), 7.90-8.14 (m, 2H), 8.50 (d, J=12.5, 2H), 9.05 (dd, J=14.60, 1.98 Hz, 2H), 10.25 (s, 1H); ESIMS found C$_{23}$H$_{24}$N$_4$O$_3$ m/z 405 (M+H).

Step c

A solution of N-(cyclopropylmethyl)-5-(3-formyl-1-(tetrahydro-2H-pyran-2-yl)-1H-indazol-5-yl)nicotinamide (XXXI) (0.404 g, 1.0 mmol), 3,3'-bipyridine-4,5-diamine (XV) (186 mg, 1.0 mmol) and sulfur (35 mg, 1.1 mmol) in dry DMF (10 mL) was heated at 140° C. overnight. The reaction was cooled and evaporated under vacuum. The residue was suspended in water, sonicated and filtered. The solid was washed with cold water and dried under vacuum. The crude product was dissolved in DCM and cooled to 4° C. overnight to get N-(cyclopropylmethyl)-5-(3-(7-(pyridin-3-yl)-3H-imidazo[4,5-c]pyridin-2-yl)-1-(tetrahydro-2H- pyran-2-yl)-1H-indazol-5-yl) nicotinamide (XXXII) as a brown solid (130 mg, 0.23 mmol, 23% yield). $^1$H NMR (DMSO-d$_6$) δ ppm 0.19-0.37 (m, 2H), 0.36-0.58 (m, 2H), 0.97-1.115 (m, 1H), 1.67 (br, 2H), 2.14 (d, J=9.98 Hz, 2H), 2.40-2.46 (m, 1H), 3.20-3.33 (m, 3H), 3.75-4.14 (m, 2H), 6.13 (d, J=8.29 Hz, 1H), 7.60 (dd, J=7.82, 4.80 Hz, 1H), 7.92-8.12 (m, 3H), 8.20 (d, J=8.67 Hz, 1H), 8.55-8.67 (m, 2H), 8.94 (br s, 3H), 9.06 (d, J=1.88 Hz, 1H), 9.19 (d, J=1.87 Hz, 1H); ESIMS found C$_{33}$H$_{30}$N$_8$O$_2$ m/z 571 (M+H).

Step d

A solution of N-(cyclopropylmethyl)-5-(3-(7-(pyridin-3-yl)-3H-imidazo[4,5-c]pyridin-2-yl)-1-(tetrahydro-2H-pyran-2-yl)-1H-indazol-5-yl) nicotinamide (XXXII) (125 mg, 0.22 mmol) and Et$_3$SiH (87 μL, 0.55 mmol) in DCM (5 mL) was slowly added TFA (2.5 mL). The reaction was stirred at r.t. for 3 h. The reaction was evaporated under vacuum and the residue was treated with water, basified with aq. ammonia. The solids were filtered, washed with cold water and dried. The crude product was heated in MeOH and filtered hot to remove impurities. The hot MeOH solution was allowed to slowly cool to r.t. to produce N-(cyclopropylmethyl)-5-(3-(7-(pyridin-3-yl)-3H-imidazo[4,5-c]pyridin-2-yl)-1H-indazol-5-yl)nicotinamide (3) as a off-white solid (48 mg, 0.10 mmol, 44% yield). $^1$H NMR (DMSO-d$_6$) δ ppm 0.28 (d, J=4.28 Hz, 2H), 0.42-0.58 (m, 2H), 1.09 (br s, 1H), 3.25 (t, J=6.06 Hz, 2H), 7.50-7.70 (m, 1H), 7.79-8.11 (m, 2H), 8.48-8.68 (m, 1H), 8.69-8.82 (m, 1H), 8.81-8.97 (m, 3H), 9.00-9.18 (m, 2H), 9.46 (br s, 1H); ESIMS found C$_{28}$H$_{22}$N$_8$O m/z 487 (M+H).

The following compounds was prepared in accordance with the procedure described in the above Example 1.

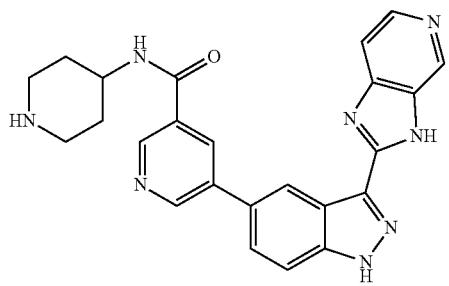 [SMILES: O=C(NC1CCNCC1)c1cncc(-c2ccc3[nH]nc(-c4nc5ccncc5[nH]4)c3c2)c1]

1

5-(3-(3H-imidazo[4,5-c]pyridin-2-yl)-1H-indazol-5-yl)-N-(piperidin-4-yl)nicotinamide 1

$^1$H NMR (DMSO-d$_6$) δ ppm 1.55-1.75 (m, 2H), 1.90-2.05 (m, 2H), 2.78-2.90 (t, 2H), 3.15-3.25 (d, 2H), 3.95-4.12 (m, 1H), 7.65 (br s, 1H), 7.87 (dd, 2H), 8.31 (d, 1H), 8.53 (s, 1H), 8.79 (s, 1H), 8.98 (s, 2H), 9.13 (s, 1H); ESIMS found for C$_{24}$H$_{22}$N$_8$O m/z 439 (M+H).

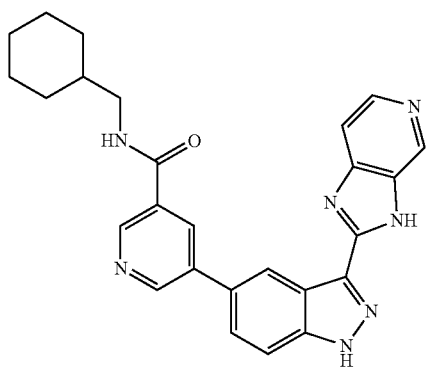 [SMILES: O=C(NCC1CCCCC1)c1cncc(-c2ccc3[nH]nc(-c4nc5ccncc5[nH]4)c3c2)c1]

2

5-(3-(3H-imidazo[4,5-c]pyridin-2-yl)-1H-indazol-5-yl)-N-(cyclohexyl methyl)nicotinamide 2

$^1$H NMR (DMSO-d$_6$) δ ppm 0.98-1.15 (m, 2H), 1.2-1.39 (m, 3H), 1.64-1.89 (m, 6H), 3.21-3.35 (m, 2H), 7.73 (d, 1H), 7.82 (d, 1H), 7.88 (d, 1H), 8.34 (s, 1H), 8.62 (s, 1H), 8.86 (s, 1H), 8.96 (s, 1H), 8.99 (s, 1H), 9.12 (s, 1H); ESIMS found for C$_{26}$H$_{25}$N$_7$O m/z 452 (M+H).

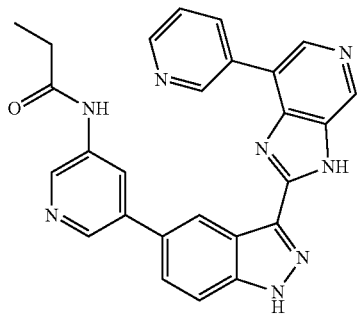 [SMILES: CCC(=O)Nc1cncc(-c2ccc3[nH]nc(-c4nc5c(-c6cccnc6)cncc5[nH]4)c3c2)c1]

4

N-(5-(3-(7-(pyridin-3-yl)-3H-imidazo[4,5-c]pyridin-2-yl)-1H-indazol-5-yl)pyridin-3-yl)propionamide 4

$^1$H NMR (DMSO-d$_6$) δ ppm 1.15 (t, J=7.16 Hz, 3H), 2.40 (q, 2H), 7.60 (br s, 1H), 7.85 (br s, 3H), 8.39-8.54 (m, 1H), 8.66 (br s, 2H), 8.77 (s, 1H), 8.82 (s, 1H), 8.97 (br s, 1H). ESIMS found for C$_{26}$H$_{20}$N$_8$O m/z 461 (M+H).

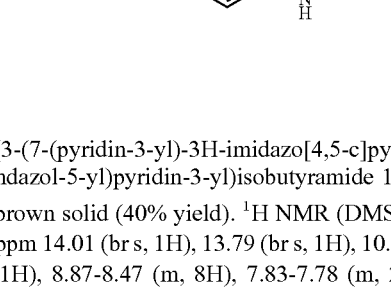

11

N-(5-(3-(7-(pyridin-3-yl)-3H-imidazo[4,5-c]pyridin-2-yl)-1H-indazol-5-yl)pyridin-3-yl)isobutyramide 11

Dark brown solid (40% yield). $^1$H NMR (DMSO-d$_6$, 400 MHz) δ ppm 14.01 (br s, 1H), 13.79 (br s, 1H), 10.19 (s, 1H), 9.42 (s, 1H), 8.87-8.47 (m, 8H), 7.83-7.78 (m, 2H), 7.57-7.54 (m, 1H), 2.69-2.62 (m, 2H), 1.14-1.13 (d, J=6.8 Hz, 6H). ESIMS found C$_{27}$H$_{22}$N$_8$O m/z 475.10 (M+H).

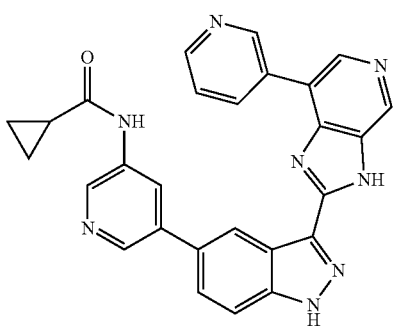

12

N-(5-(3-(7-(pyridin-3-yl)-3H-imidazo[4,5-c]pyridin-2-yl)-1H-indazol-5-yl)pyridin-3-yl)cyclopropanecarboxamide 12

Dark brown solid (23% yield). $^1$H NMR (DMSO-d$_6$, 400 MHz) δ ppm 14.03 (s, 1H), 13.80 (s, 1H), 10.59 (s, 1H), 9.45 (s, 1H), 8.92-8.65 (m 7H), 8.47 (s, 1H), 7.83 (s, 2H), 7.57 (s, 1H), 1.88-1.86 (m, 1H), 0.88-0.87 (m, 4H). ESIMS found C$_{27}$H$_{20}$N$_8$O m/z 473.15 (M+H).

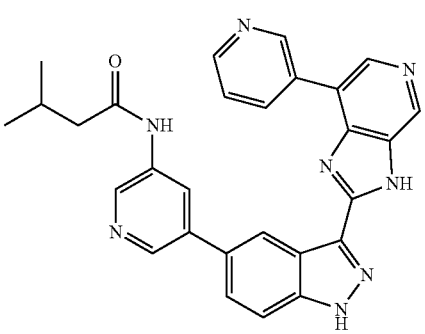 [SMILES: CC(C)CC(=O)Nc1cncc(-c2ccc3[nH]nc(-c4nc5c(-c6cccnc6)cncc5[nH]4)c3c2)c1]

15

3-methyl-N-(5-(3-(7-(pyridin-3-yl)-3H-imidazo[4,5-c]pyridin-2-yl)-1H-indazol-5-yl)pyridin-3-yl)butanamide 15

Dark brown solid (14% yield). $^1$H NMR (DMSO-d$_6$, 400 MHz) δ ppm 14.03 (s, 1H), 13.78 (br s, 1H), 10.24 (s, 1H), 9.46 (s, 1H), 8.89-8.76 (m, 4H), 8.75-8.39 (m, 4H), 7.86-7.82 (m, 2H), 7.59-7.58 (m, 1H), 2.30-2.28 (d, J=6.8 Hz, 2H), 2.18-2.12 (m, 1H), 0.99-097 (d, J=6.4 Hz, 6H). ESIMS found C$_{28}$H$_{24}$N$_8$O m/z 489.20 (M+H).

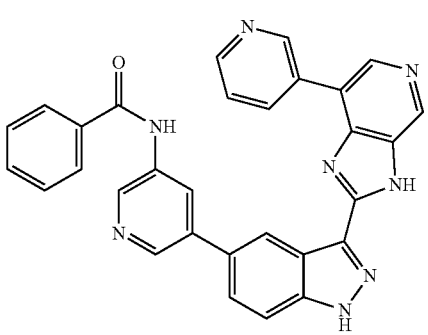

16

N-(5-(3-(7-(pyridin-3-yl)-3H-imidazo[4,5-c]pyridin-2-yl)-1H-indazol-5-yl)pyridin-3-yl)benzamide 16

Dark brown solid (30% yield). $^1$H NMR (DMSO-d$_6$, 400 MHz) δ ppm 14.04 (s, 1H), 13.80 (s, 1H), 10.63 (s, 1H), 9.45 (s, 1H), 9.00-8.74 (m, 6H), 8.63 (s, 1H), 8.36 (s, 1H), 8.07-8.05 (m, 2H), 7.88-7.86 (m, 2H), 7.67-7.52 (m, 4H). ESIMS found C$_{30}$H$_{20}$N$_8$O m/z 509.05 (M+H).

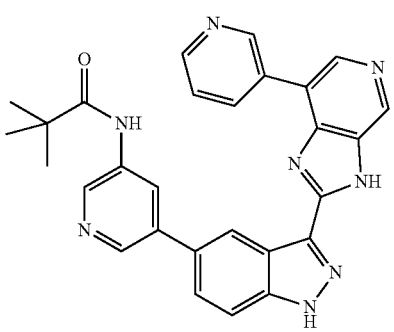

17

N-(5-(3-(7-(pyridin-3-yl)-3H-imidazo[4,5-c]pyridin-2-yl)-1H-indazol-5-yl)pyridin-3-yl)pivalamide 17

Dark brown solid (43% yield). $^1$H NMR (DMSO-d$_6$, 400 MHz) δ ppm 14.03 (s, 1H), 13.79 (br s, 1H), 9.57 (s, 1H), 9.46 (s, 1H), 8.92-8.81 (m, 4H), 8.75-8.49 (m, 4H), 7.84 (s, 2H), 7.59-7.56 (m, 1H), 1.29 (s, 9H). ESIMS found C$_{28}$H$_{24}$N$_8$O m/z 489.15 (M+H).

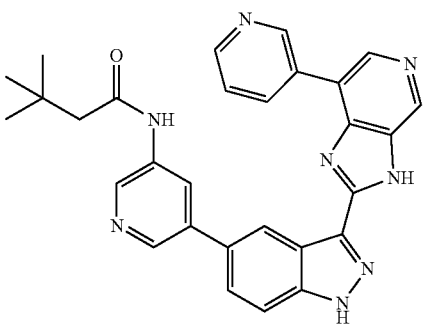 [SMILES: CC(C)(C)CC(=O)Nc1cncc(-c2ccc3[nH]nc(-c4nc5c(-c6cccnc6)cncc5[nH]4)c3c2)c1]

18

3,3-dimethyl-N-(5-(3-(7-(pyridin-3-yl)-3H-imidazo[4,5-c]pyridin-2-yl)-1H-indazol-5-yl)pyridin-3-yl)butanamide 18

Dark brown solid (32% yield). $^1$H NMR (DMSO-d$_6$, 400 MHz) δ ppm 14.03 (s, 1H), 13.77 (s, 1H), 10.18 (s, 1H), 9.46 (s, 1H), 8.89-8.75 (m, 4H), 8.65-8.40 (m, 2H), 7.86-7.79 (m, 2H), 7.59-7.56 (m, 2H), 2.29 (s, 2H), 1.06 (s, 9H). ESIMS found C$_{29}$H$_{26}$N$_8$O m/z 503.15 (M+H).

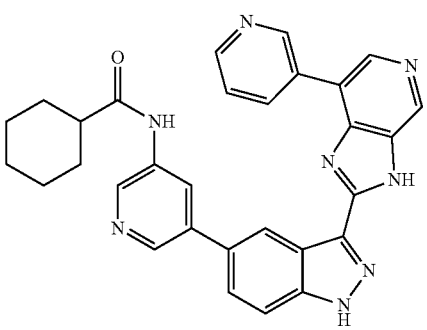 [SMILES: O=C(Nc1cncc(-c2ccc3[nH]nc(-c4nc5c(-c6cccnc6)cncc5[nH]4)c3c2)c1)C1CCCCC1]

N-(5-(3-(7-(pyridin-3-yl)-3H-imidazo[4,5-c]pyridin-2-yl)-1H-indazol-5-yl)pyridin-3-yl)cyclohexanecarboxamide 19

Off white solid (17% yield). $^1$H NMR (DMSO-d$_6$, 400 MHz) δ ppm 14.04 (s, 1H), 13.78 (s, 1H), 10.20 (s, 1H), 9.45 (s, 1H), 8.89-8.51 (m, 7H), 7.83 (s, 2H), 7.59 (s, 2H), 1.90-1.66 (m, 5H), 1.47-1.22 (m, 6H). ESIMS found C$_{30}$H$_{26}$N$_8$O m/z 515.15 (M+H).

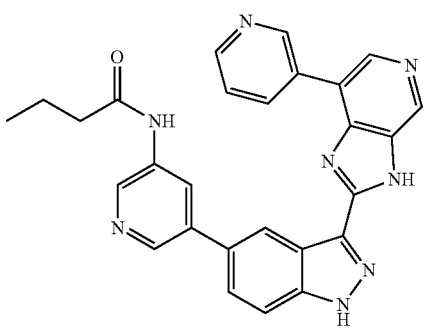 [SMILES: CCCC(=O)Nc1cncc(-c2ccc3[nH]nc(-c4nc5c(-c6cccnc6)cncc5[nH]4)c3c2)c1]

N-(5-(3-(7-(pyridin-3-yl)-3H-imidazo[4,5-c]pyridin-2-yl)-1H-indazol-5-yl)pyridin-3-yl)butyramide 20

Dark brown solid (34% yield). $^1$H NMR (DMSO-d$_6$, 400 MHz) δ ppm 14.07 (s, 1H), 10.26 (s, 1H), 9.40 (s, 1H), 8.96 (s, 1H), 8.80-8.65 (m, 6H), 8.48 (s, 2H), 7.87-7.81 (m, 2H), 7.62-7.59 (m, 1H), 2.41-2.38 (t, J=7.2 Hz, 2H), 1.70-1.64 (m, 2H), 0.98-0.94 (t, J=7.2 Hz, 3H). ESIMS found C$_{27}$H$_{22}$N$_8$O m/z 475.10 (M+H).

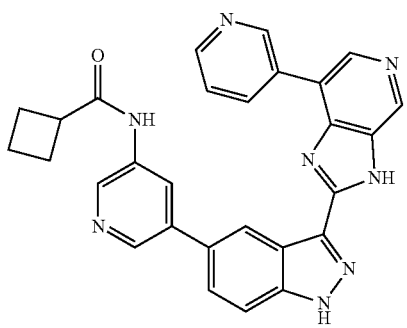 [SMILES: O=C(Nc1cncc(-c2ccc3[nH]nc(-c4nc5c(-c6cccnc6)cncc5[nH]4)c3c2)c1)C1CCC1]

N-(5-(3-(7-(pyridin-3-yl)-3H-imidazo[4,5-c]pyridin-2-yl)-1H-indazol-5-yl)pyridin-3-yl)cyclobutanecarboxamide 21

Off white solid (21% yield). $^1$H NMR (DMSO-d$_6$, 400 MHz) δ ppm 13.09 (s, 1H), 13.06 (s, 1H), 10.11 (s, 1H), 9.43 (bs, 1H), 8.92-8.78 (m 6H), 8.49 (s, 2H), 7.82 (s, 2H), 7.58-7.56 (m, 1H), 2.31-2.27 (m, 4H), 2.19-2.17 (m, 2H), 2.02-1.95 (m, 1H). ESIMS found C$_{28}$H$_{22}$N$_8$O m/z 487.10 (M+H).

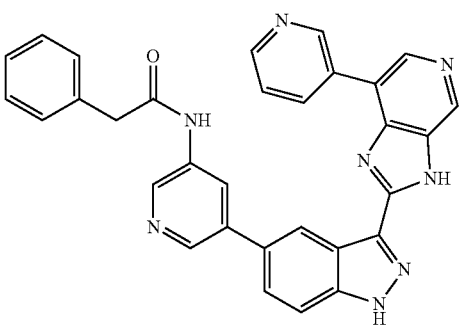 [SMILES: O=C(Cc1ccccc1)Nc1cncc(-c2ccc3[nH]nc(-c4nc5c(-c6cccnc6)cncc5[nH]4)c3c2)c1]

2-phenyl-N-(5-(3-(7-(pyridin-3-yl)-3H-imidazo[4,5-c]pyridin-2-yl)-1 H-indazol-5-yl)pyridin-3-yl)acetamide 22

Off white solid (40% yield). $^1$H NMR (DMSO-d$_6$, 400 MHz) δ ppm 13.99 (s, 1H), 13.00 (s, 1H), 10.58 (s, 1H), 9.41 (s, 1H), 8.90-8.49 (m, 8H), 7.85-7.83 (m, 2H), 7.52-7.27 (m, 6H), 3.76 (s, 2H). ESIMS found C$_{31}$H$_{22}$N$_8$O m/z 523.15 (M+H).

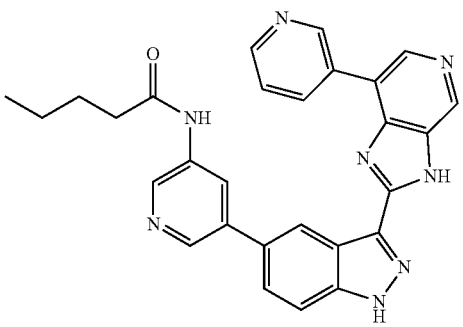 [SMILES: CCCCC(=O)Nc1cncc(-c2ccc3[nH]nc(-c4nc5c(-c6cccnc6)cncc5[nH]4)c3c2)c1]

N-(5-(3-(7-(pyridin-3-yl)-3H-imidazo[4,5-c]pyridin-2-yl)-1H-indazol-5-yl)pyridin-3-yl)pentanamide 23

Dark brown solid (28% yield). $^1$H NMR (DMSO-d$_6$, 400 MHz) δ ppm 14.05 (s, 1H), 13.01 (s, 1H), 10.26 (s, 1H), 9.39 (s, 1H), 8.95-8.65 (m, 7H), 8.47 (s, 1H), 7.86-7.80 (m, 2H), 7.61-7.58 (m, 1H), 2.43-2.40 (t, J=7.2 Hz, 2H), 1.65-1.59 (m, 2H), 1.40-1.34 (m, 2H), 0.94-0.90 (t, J=7.2 Hz, 3H). ESIMS found C$_{28}$H$_{24}$N$_8$O m/z 489.15 (M+H).

Administration and Pharmaceutical Compositions

Some embodiments include pharmaceutical compositions comprising: (a) a safe and therapeutically effective amount of the indazole, or its corresponding enantiomer, diastereoisomer or tautomer, or pharmaceutically acceptable salt; and (b) a pharmaceutically acceptable carrier.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications.

Compounds of the invention intended for pharmaceutical use may be administered as crystalline or amorphous products. Pharmaceutically acceptable compositions include solid, semi-solid, liquid and aerosol dosage forms, such as, e.g., tablets, capsules, powders, liquids, suspensions, suppositories, aerosols or the like. They may be obtained, for example, as films by methods such as precipitation, crystallization, freeze drying, spray drying, or evaporative drying. Microwave or radio frequency drying may be used for this purpose. The compounds can also be administered in sustained or controlled release dosage forms, including depot injections, osmotic pumps, pills, transdermal (including electrotransport) patches, and the like, for prolonged and/or timed, pulsed administration at a predetermined rate. Preferably, the compositions are provided in unit dosage forms suitable for single administration of a precise dose.

The compounds can be administered either alone or more typically in combination with a conventional pharmaceutical carrier, excipient or the like. The term "excipient" is used herein to describe any ingredient other than the compound(s) of the invention. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β-, and γ-cyclodextrin, or chemically modified derivatives such as hydroxyalkylcyclodextrins, including 2- and 3-hydroxypropyl-b-cyclodextrins, or other solubilized derivatives can also be advantageously used to enhance delivery of compounds of the formulae described herein. Dosage forms or compositions containing a compound as described herein in the range of 0.005% to 100% with the balance made up from non-toxic carrier may be prepared. The contemplated compositions may contain 0.001%-100% active ingredient, in one embodiment 0.1-95%, in another embodiment 75-85%. Actual methods of preparing such dosage forms are known, or will be apparent, to those skilled in this art; for example, see *Remington: The Science and Practice of Pharmacy*, 21st Edition (Lippincott Williams & Wilkins. 2005).

In one preferred embodiment, the compositions will take the form of a unit dosage form such as a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule. Unit dosage forms in which the two active ingredients are physically separated are also contemplated; e.g., capsules with granules of each drug; two-layer tablets; two-compartment gel caps, etc.

Liquid pharmaceutically administrable compositions can, for example, be prepared by dissolving, dispersing, etc. an active compound as defined above and optional pharmaceutical adjuvants in a carrier (e.g., water, saline, aqueous dextrose, glycerol, glycols, ethanol or the like) to form a solution or suspension. If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Injectables can be prepared in conventional forms, either as liquid solutions or suspensions, as emulsions, or in solid forms suitable for dissolution or suspension in liquid prior to injection. The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid, which will be subsequently diluted to the above percentages. In some embodiments, the composition will comprise 0.2-2% of the active agent in solution.

It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Solid compositions can be provided in various different types of dosage forms, depending on the physicochemical properties of the drug, the desired dissolution rate, cost considerations, and other criteria. In one of the embodiments, the solid composition is a single unit. This implies that one unit dose of the drug is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In a preferred embodiment, the solid composition is a highly porous lyophilized form. Such lyophilizates, sometimes also called wafers or lyophilized tablets, are particularly useful for their rapid disintegration, which also enables the rapid dissolution of the active compound.

On the other hand, for some applications the solid composition may also be formed as a multiple unit dosage form as defined above. Examples of multiple units are powders, granules, microparticles, pellets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution.

Another type of multiparticulate system which is also capable of achieving rapid drug dissolution is that of powders, granules, or pellets from water-soluble excipients which are coated with the drug, so that the drug is located at the outer surface of the individual particles. In this type of system, the water-soluble low molecular weight excipient is useful for preparing the cores of such coated particles, which can be subsequently coated with a coating composition comprising the drug and, preferably, one or more additional excipients, such as a binder, a pore former, a saccharide, a sugar alcohol, a film-forming polymer, a plasticizer, or other excipients used in pharmaceutical coating compositions.

Also provided herein are kits. Typically, a kit includes one or more compounds or compositions as described herein. In certain embodiments, a kit can include one or more delivery systems, e.g., for delivering or administering a compound as provided above, and directions for use of the kit (e.g., instructions for treating a patient). In another embodiment, the kit can include a compound or composition as described herein and a label that indicates that the contents are to be administered to a patient with cancer. In another embodiment, the kit can include a compound or composition as described herein and a label that indicates that the contents are to be administered to a patient with one or more of hepatocellular carcinoma, colon cancer, leukemia, lymphoma, sarcoma, ovarian cancer, diabetic retinopathy, neovascular glaucoma, rheumatoid arthritis, psoriasis, mycotic and viral infections, osteochondrodysplasia, Alzheimer's disease, osteoarthritis, polyposis *coli*, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome and Rett syndrome.

The actual dose of the active compounds of the present invention depends on the specific compound, and on the condition to be treated; the selection of the appropriate dose is well within the knowledge of the skilled artisan.

Methods of Treatment

The compounds and compositions provided herein can be used as inhibitors of one or more members of the Wnt pathway, including one or more Wnt proteins, and thus can be used to treat a variety of disorders and diseases in which aberrant Wnt signaling is implicated, such as cancer and other diseases associated with abnormal angiogenesis, cellular proliferation, and cell cycling. Accordingly, the compounds and compositions provided herein can be used to treat cancer, to reduce or inhibit angiogenesis, to reduce or inhibit cellular proliferation and correct an genetic disorder due to mutations in Wnt signaling components. Non-limiting examples of diseases which can be treated with the compounds and compositions provided herein include a variety of cancers, diabetic retinopathy, neovascular glaucoma, rheumatoid arthritis, psoriasis, mycotic and viral infections, osteochondrodysplasia, Alzheimer's disease, osteoarthritis, polyposis *coli*, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome and Rett syndrome.

With respect to cancer, the Wnt pathway is known to be constitutively activated in a variety of cancers including, for example, colon cancer, hepatocellular carcinoma, lung cancer, ovarian cancer, prostate cancer, pancreatic cancer and leukemias such as CML, CLL and T-ALL. The constitutive activation is due to constitutively active β-catenin, perhaps due to its stabilization by interacting factors or inhibition of the degradation pathway. Accordingly, the compounds and compositions described herein may be used to treat these cancers in which the Wnt pathway is constitutively activated. In certain embodiments, the cancer is chosen from hepatocellular carcinoma, colon cancer, leukemia, lymphoma, sarcoma and ovarian cancer.

Other cancers can also be treated with the compounds and compositions described herein.

More particularly, cancers that may be treated by the compound, compositions and methods described herein include, but are not limited to, the following:

1) Breast cancers, including, for example $ER^+$ breast cancer, $ER^-$ breast cancer, $her2^-$ breast cancer, $her2^+$ breast cancer, stromal tumors such as fibroadenomas, phyllodes tumors, and sarcomas, and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative ($ER^-$), progesterone receptor negative, and her2 negative ($her2^-$). In some embodiments, the breast cancer may have a high risk Oncotype score.

2) Cardiac cancers, including, for example sarcoma, e.g., angiosarcoma, fibrosarcoma, rhabdomyosarcoma, and liposarcoma; myxoma; rhabdomyoma; fibroma; lipoma and teratoma.

3) Lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma.

4) Gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.

5) Genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.

6) Liver cancers, including, for example, hepatoma, e.g., hepatocellular carcinoma; cholangiocarcinoma; hepatoblastoma; angiosarcoma; hepatocellular adenoma; and hemangioma.

7) Bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.

8) Nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma.

9) Gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa theca cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma.

10) Hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenström's macroglobulinemia.

11) Skin cancers and skin disorders, including, for example, malignant melanoma, basal cell carcinoma, squamous cell carcinoma, Kaposi's sarcoma, moles dysplastic nevi, lipoma, angioma, dermatofibroma, keloids, and psoriasis.

12) Adrenal gland cancers, including, for example, neuroblastoma.

Cancers may be solid tumors that may or may not be metastatic. Cancers may also occur, as in leukemia, as a diffuse tissue. Thus, the term "tumor cell," as provided herein, includes a cell afflicted by any one of the above identified disorders.

A method of treating cancer using a compound or composition as described herein may be combined with existing methods of treating cancers, for example by chemotherapy, irradiation, or surgery (e.g., oophorectomy). In some embodiments, a compound or composition can be administered before, during, or after another anticancer agent or treatment.

The compounds and compositions described herein can be used as anti-angiogenesis agents and as agents for modulating and/or inhibiting the activity of protein kinases, thus providing treatments for cancer and other diseases associated with cellular proliferation mediated by protein kinases. For example, the compounds described herein can inhibit the activity of one or more kinases, such as CDKs, VEGF, CLK, HIPK, Abl, JAK and CHK-1, or cyclin complexes thereof. Accordingly, provided herein is a method of treating cancer or preventing or reducing angiogenesis through kinase inhibition, such as through inhibition of VEGF, CHK-1, CLK, HIPK, Abl, JAK, CDK4 or CDK4/D-type cyclin complexes and/or CDK2 or CDK2/E-type cyclin complexes.

In addition, and including treatment of cancer, the compounds and compositions described herein can function as cell-cycle control agents for treating proliferative disorders in a patient. Disorders associated with excessive proliferation include, for example, cancers, psoriasis, immunological disorders involving undesired proliferation of leukocytes, and restenosis and other smooth muscle disorders. Furthermore, such compounds may be used to prevent de-differentiation of post-mitotic tissue and/or cells.

Diseases or disorders associated with uncontrolled or abnormal cellular proliferation include, but are not limited to, the following:

a variety of cancers, including, but not limited to, carcinoma, hematopoietic tumors of lymphoid lineage, hematopoietic tumors of myeloid lineage, tumors of mesenchymal origin, tumors of the central and peripheral nervous system and other tumors including melanoma, seminoma and Kaposi's sarcoma.

a disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

defective apoptosis-associated conditions, such as cancers (including but not limited to those types mentioned hereinabove), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus erythematosus, rheumatoid arthritis, psoriasis, autoimmune mediated glomerulonephritis, inflammatory bowel disease and autoimmune diabetes mellitus), neurodegenerative disorders (including but not limited to Alzheimer's disease, amyotrophic lateral sclerosis, retinitis pigmentosa, Parkinson's disease, AIDS-related dementia, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteroporosis and arthritis), aspirin-sensitive rhinosinusitis, cystic fibrosis, multiple sclerosis, kidney diseases and cancer pain.

genetic diseases due to mutations in Wnt signaling components, such as polyposis *coli*, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/

Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome and Rett syndrome.

The compounds and compositions may also be useful in the inhibition of the development of invasive cancer, tumor angiogenesis and metastasis.

Moreover, the compounds and compositions, for example, as inhibitors of the CDKs, can modulate the level of cellular RNA and DNA synthesis and therefore are expected to be useful in the treatment of viral infections such as HIV, human papilloma virus, herpes virus, Epstein-Barr virus, adenovirus, Sindbis virus, pox virus and the like.

Compounds and compositions described herein can inhibit the kinase activity of, for example, CDK/cyclin complexes, such as those active in the $G_0$ or $G_{-1}$ stage of the cell cycle, e.g., CDK2, CDK4, and/or CDK6 complexes.

Evaluation of Biological Activity

The biological activity of the compounds described herein can be tested using any suitable assay known to those of skill in the art, e.g., WO 2001/053268 or WO 2005/009997. For example, the activity of a compound may be tested using one or more of the test methods outlined below.

In one example, tumor cells may be screened for Wnt independent growth. In such a method, tumor cells of interest are contacted with a compound (i.e. inhibitor) of interest, and the proliferation of the cells, e.g. by uptake of tritiated thymidine, is monitored. In some embodiments, tumor cells may be isolated from a candidate patient who has been screened for the presence of a cancer that is associated with a mutation in the Wnt signaling pathway. Candidate cancers include, without limitation, those listed above.

In another example, one may utilize in vitro assays for Wnt biological activity, e.g. stabilization of β-catenin and promoting growth of stem cells. Assays for biological activity of Wnt include stabilization of β-catenin, which can be measured, for example, by serial dilutions of a candidate inhibitor composition. An exemplary assay for Wnt biological activity contacts a Wnt composition in the presence of a candidate inhibitor with cells, e.g. mouse L cells. The cells are cultured for a period of time sufficient to stabilize β-catenin, usually at least about 1 hour, and lysed. The cell lysate is resolved by SDS PAGE, then transferred to nitrocellulose and probed with antibodies specific for β-catenin.

In a further example, the activity of a candidate compound can be measured in a *Xenopus* secondary axis bioassay (Leyns, L. et al. *Cell* (1997), 88(6), 747-756).

Example 2

Another screening assay for Wnt activity is described as follows. Reporter cell lines can be generated by stably transducing cells of cancer cell lines (e.g., colon cancer) with a lentiviral construct that include a wnt-responsive promoter driving expression of the firefly luciferase gene.

Lentiviral constructs can be made in which the SP5 promoter, a promoter having eight TCF/LEF binding sites derived from the SP5 promoter, is linked upstream of the firefly luciferase gene. The lentiviral constructs can also include a hygromycin resistance gene as a selectable marker. The SP5 promoter construct can be used to transduce SW480 cells, a colon cancer cell line having a mutated APC gene that generates a truncated APC protein, leading to de-regulated accumulation of β-catenin. A control cell line can be generated using another lentiviral construct containing the luciferase gene under the control of the SV40 promoter which does not require β-catenin for activation.

Cultured SW480 cells bearing a reporter construct can be distributed at approximately 10,000 cells per well into 384 well multiwell plates. Compounds from a small molecule compound library can then be added to the wells in half-log dilutions using a three micromolar top concentration. A series of control wells for each cell type receive only buffer and compound solvent. Twenty-four hours after the addition of compound, reporter activity for luciferases can be assayed, for example, by addition of the BrightGlo luminescence reagent (Promega) and the Victor3 plate reader (Perkin Elmer). Readings can be normalized to DMSO only treated cells, and normalized activities can then be used in the $IC_{50}$ calculations. Table 2 shows the activity of selected indazole analogs.

TABLE 2

| Compound | Wnt inhibition, $IC_{50}$ |
|---|---|
| 1 | >10 µM |
| 2 | >10 µM |
| 3 | >10 µM |
| 4 | 29-50 nM |
| 11 | 4 nM |
| 12 | 26-35 nM |
| 15 | 5.6 nM |
| 16 | 0.38-1.17 µM |
| 17 | 32- 50 nM |
| 18 | 21-39 nM |
| 19 | 86-206 nM |
| 20 | 63 nM |
| 21 | 29 nM |
| 23 | 34-64 nM |

The term "comprising" as used herein is synonymous with "including," "containing," or "characterized by," and is inclusive or open-ended and does not exclude additional, unrecited elements or method steps.

What is claimed is:

1. A method of treating a genetic disease caused by mutations in Wnt signaling components, wherein the genetic disease is selected from: polyposis *coli*, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome and Rett syndrome in a subject, the method comprising administering to the subject a therapeutically effective amount of a compound of Formula Ia, or a pharmaceutically acceptable salt thereof:

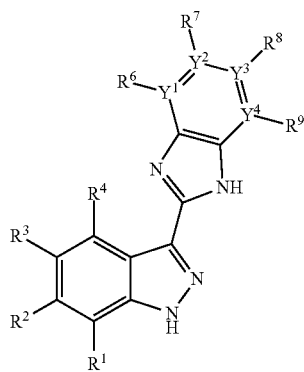

wherein:

R[1], R[2], R[4], R[6], R[7], R[8] and R[9] are independently selected from the group consisting of H, $C_{1-9}$ alkyl, halide, —CF$_3$, —($C_{1-9}$ alkyl)$_n$carbocyclylR[13], —($C_{1-9}$ alkyl)$_n$heterocyclylR[13], —($C_{1-9}$ alkyl)$_n$arylR[13], —($C_{1-9}$ alkyl)$_n$heteroarylR[13], —($C_{1-9}$ alkyl)$_n$OR[10], —($C_{1-9}$ alkyl)$_n$SR[10], —($C_{1-9}$ alkyl)$_n$S(=O)R[11], —($C_{1-9}$ alkyl)$_n$SO$_2$R[10], —($C_{1-9}$ alkyl)$_n$N(R[10])SO$_2$R[10], —($C_{1-9}$ alkyl)$_n$SO$_2$N(R[10])$_2$, —($C_{1-9}$ alkyl)$_n$N(R[10])$_2$, —($C_{1-9}$ alkyl)$_n$N(R[10])C(=A)N(R[10])$_2$, —($C_{1-9}$ alkyl)$_n$C(=A)N(R[10])$_2$, —($C_{1-9}$ alkyl)$_n$N(R[10])C(=A)R[10], —NO$_2$, —CN, —($C_{1-9}$ alkyl)$_n$CO$_2$R[10], and —($C_{1-9}$ alkyl)$_n$C(=A)R[10];

R[3] is selected from the group consisting of —NRS(=O)R[14], —($C_{1-9}$ alkyl)R[14], -carbocyclylR[14]R[15], -heterocyclylR[14]R[15], -arylR[14]R[15], and -heteroarylR[14]R[15];

alternatively, one of each of R[1] and R[2], R[2] and R[3], R[3] and R[4], R[6] and R[7], R[7] and R[8] or R[8] and R[9] are taken together to form a ring which is selected from the group consisting of aryl, heteroaryl,

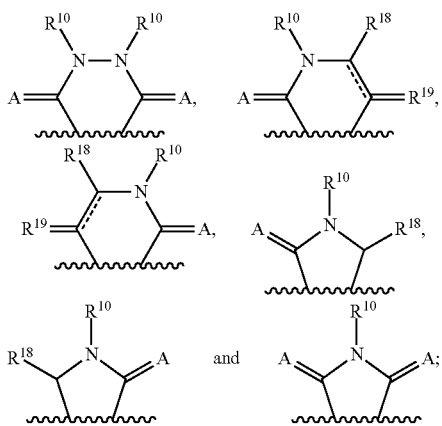

wherein each bond represented by a dashed and solid line represents a bond selected from the group consisting of a single bond and a double bond;

each R[10] is independently selected from the group consisting of H, —$C_{1-9}$ alkyl, —CF$_3$, —($C_{1-9}$ alkyl)$_n$carbocyclyl, —($C_{1-9}$ alkyl)$_n$heterocyclyl, —($C_{1-9}$ alkyl)$_n$aryl, and —($C_{1-9}$ alkyl)$_n$heteroaryl;

each R[11] is independently selected from the group consisting of —$C_{1-9}$ alkyl, —CF$_3$, —($C_{1-9}$ alkyl)$_n$carbocyclyl, —($C_{1-9}$ alkyl)$_n$heterocyclyl, —($C_{1-9}$ alkyl)$_n$aryl, and —($C_{1-9}$ alkyl)$_n$heteroaryl;

each R[12] is independently selected from the group consisting of —OR[10] and R[10];

each R[13] is 1-5 substituents each selected from the group consisting of H, $C_{1-9}$ alkyl, halide, —CF$_3$, carbocyclyl, heterocyclyl, aryl, heteroaryl, —($C_{1-9}$ alkyl)$_n$OR[10], —($C_{1-9}$ alkyl)$_n$SR[10], —($C_{1-9}$ alkyl)$_n$S(=O)R[11], —($C_{1-9}$ alkyl)$_n$SO$_2$R[10], —($C_{1-9}$ alkyl)$_n$N(R[10])SO$_2$R[10], —($C_{1-9}$ alkyl)$_n$SO$_2$N(R[10])$_2$, —($C_{1-9}$ alkyl)$_n$N(R[10])$_2$, —($C_{1-9}$ alkyl)$_n$N(R[10])C(=A)N(R[10])$_2$, —($C_{1-9}$ alkyl)$_n$C(=A)N(R[10])$_2$, —($C_{1-9}$ alkyl)$_n$N(R[10])C(=A)R[10], —NO$_2$, —CN, —($C_{1-9}$ alkyl)$_n$CO$_2$R[10], and —($C_{1-9}$ alkyl)$_n$C(=A)R[10];

R[14] is selected from the group consisting of —NR[10]C(=A)R[10], —NR[10]S(=O)R[11], —NR[10]SO$_2$R[10], —NR[10]C(=O)N(R[16])$_2$, —NR[10]C(=S)N(R[10])$_2$, —NR[10]C(=NR[12])N(R[10])$_2$, —N(R[16])$_2$, —C(=O)NR[10]R[17], —C(=S)N(R[10])$_2$, —C(=NR[12])N(R[10])$_2$, —OC(=A)R[10], —C(=A)R[10], —NR[10]C(=A)OR[10], and —OC(=A)NR[10]R[10];

R[15] is 1-4 substituents each selected from the group consisting of H, $C_{1-9}$ alkyl, halide, —CF$_3$, carbocyclylR[13], heterocyclylR[13], arylR[13], heteroarylR[13], —($C_{1-9}$ alkyl)$_n$OR[10], —($C_{1-9}$ alkyl)$_n$SR[10], —($C_{1-9}$ alkyl)$_n$S(=O)R[11], —($C_{1-9}$ alkyl)$_n$SO$_2$R[10], —($C_{1-9}$ alkyl)$_n$N(R[10])SO$_2$R[10], —($C_{1-9}$ alkyl)$_n$SO$_2$N(R[10])$_2$, —($C_{1-9}$ alkyl)$_n$N(R[10])$_2$, —($C_{1-9}$ alkyl)$_n$N(R[10])C(=A)N(R[10])$_2$, —($C_{1-9}$ alkyl)$_n$C(=A)N(R[10])$_2$, —($C_{1-9}$ alkyl)$_n$N(R[10])C(=A)R[10], —NO$_2$, —CN, —($C_{1-9}$ alkyl)$_n$CO$_2$R[10], and —($C_{1-9}$ alkyl)$_n$C(=A)R[10];

R[16] is —$C_{1-9}$ alkyl;

each R[17] is independently selected from the group consisting of -heterocyclylR[13], —($C_{1-9}$ alkyl)heterocyclylR[13], and —($C_{1-9}$ alkyl)carbocyclylR[13];

R[18] and R[19] are independently selected from the group consisting of H, $C_{1-9}$ alkyl, halide, —($C_{1-9}$ alkyl)$_n$carbocyclylR[13], —($C_{1-9}$ alkyl)$_n$heterocyclylR[13], —($C_{1-9}$ alkyl)$_n$arylR[13], —($C_{1-9}$ alkyl)$_n$heteroarylR[13], —($C_{1-9}$ alkyl)$_n$OR[10], —($C_{1-9}$ alkyl)$_n$SR[10], —($C_{1-9}$ alkyl)$_n$S(=O)R[10], —($C_{1-9}$ alkyl)$_n$SO$_2$R[10], —($C_{1-9}$ alkyl)$_n$N(R[10])SO$_2$R[10], —($C_{1-9}$ alkyl)$_n$SO$_2$N(R[10])$_2$, —($C_{1-9}$ alkyl)$_n$N(R[10])$_2$, —($C_{1-9}$ alkyl)$_n$N(R[10])C(=A)N(R[10])$_2$, —($C_{1-9}$ alkyl)$_n$C(=A)N(R[10])$_2$, —($C_{1-9}$ alkyl)$_n$N(R[10])C(=A)R[10], —NO$_2$, —CN, —($C_{1-9}$ alkyl)$_n$CO$_2$R[10], and —($C_{1-9}$ alkyl)$_n$C(=A)R[10];

alternatively, R[18] and R[19] are taken together to form a ring which is selected from the group consisting of benzene and pyridine;

each A is independently selected from O, S, and NR[12];

Y[1], Y[2], and Y[4] are C;

Y[3] is nitrogen and R[8] is absent; and each n is 0 or 1.

2. The method of claim 1, wherein R[1], R[2] and R[4] are H and R[3] is independently selected from the group consisting of —NRS(=O)R[14], —($C_{1-9}$alkyl)R[14], -carbocyclylR[14]R[15], -heterocyclylR[14]R[15], -arylR[14]R[15] and -heteroarylR[14]R[15].

3. The method of claim 2, wherein R[3] is -heterocyclylR[14]R[15].

4. The method of claim 2, wherein R[3] is -arylR[14]R[15].

5. The method of claim 2, wherein R[3] is -heteroarylR[14]R[15].

6. The method of claim 5, wherein R[14] is —NR[10]C(=A)R[10] and A is O.

7. The method of claim 5, in which the heteroaryl is a pyridine.

8. The method of claim 7, in which R[14] is —NHC(=O)R[10] and R[10] is selected from the group consisting of —$C_{1-9}$ alkyl, carbocyclyl, aryl and —($C_{1-9}$ alkyl)aryl.

9. The method of claim 6, in which $R^{14}$ is —C(=O)NHR$^{17}$, $R^{17}$ is —(C$_{1-9}$ alkyl)carbocyclylR$^{13}$ and $R^{13}$ is H.

10. The method of claim 1, wherein $R^6$ is —(C$_{1-9}$ alkyl)$_n$heteroarylR$^{13}$, n is 0 and $R^{13}$ is H.

11. The method of claim 1, wherein $R^1$, $R^2$, $R^4$, $R^7$, and $R^9$ are H; $R^3$ is heteroarylR$^{14}$R$^{15}$; and $R^6$ is —(C$_{1-9}$ alkyl)$_n$arylR$^{13}$.

12. The method of claim 11, in which $R^{14}$ is —NHC(=O)R$^{10}$ and $R^{10}$ is selected from the group consisting of —C$_{1-9}$ alkyl, carbocyclyl, aryl and —(C$_{1-9}$ alkyl)aryl.

13. The method of claim 12, wherein $R^{13}$ is fluoro.

14. The method of claim 1, wherein the genetic disease is diabetes mellitus type 2.

15. The method of claim 1, wherein the genetic disease is obesity.

16. The method of claim 1, wherein the genetic disease is familial exudative vitreoretinopathy.

17. The method of claim 1, wherein the genetic disease is retinal angiogenesis.

18. The method of claim 1, wherein the genetic disease is neural tube defects.

19. The method of claim 1, wherein the subject is a human.

20. The method of claim 1, wherein the compound of Formula Ia is selected from the group consisting of:

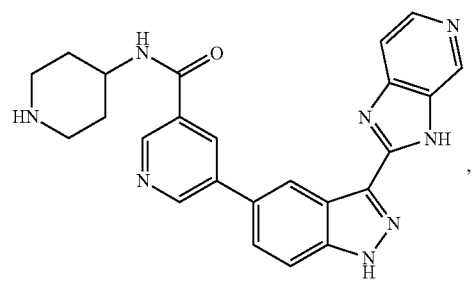

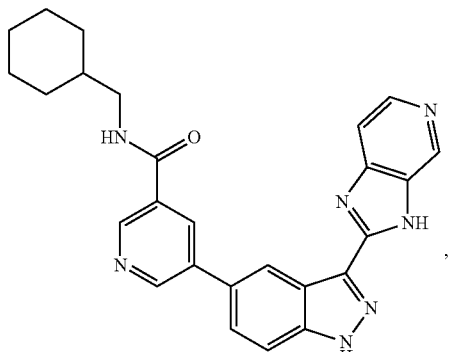

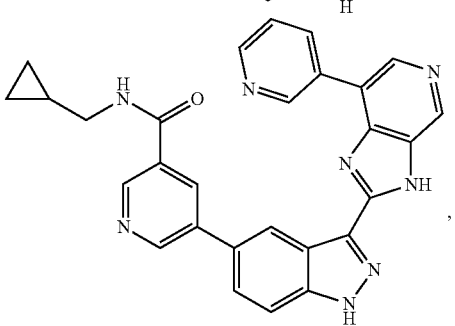

-continued

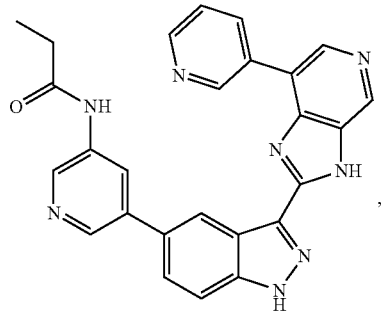

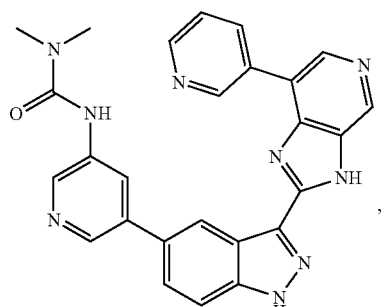

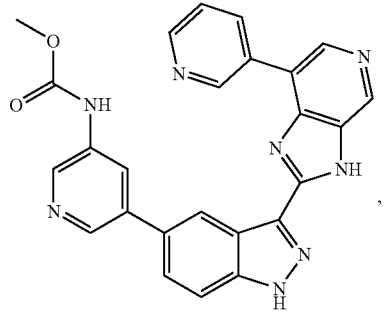

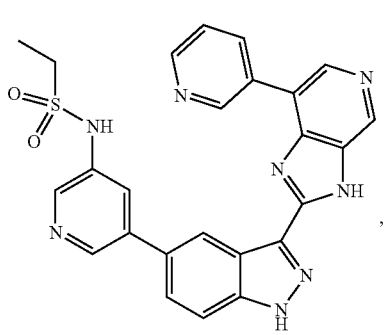

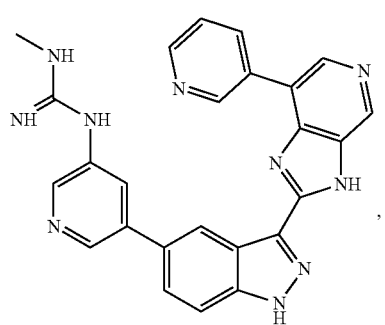

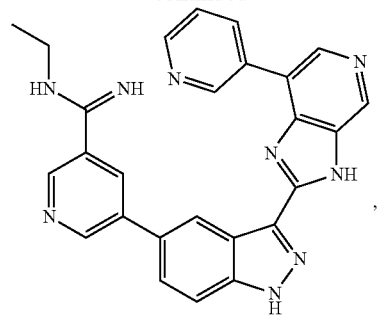,
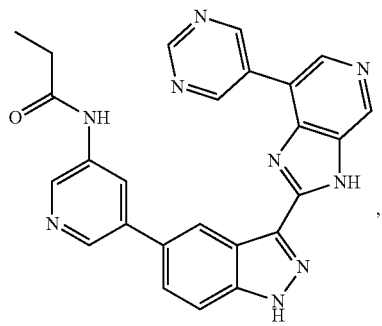,
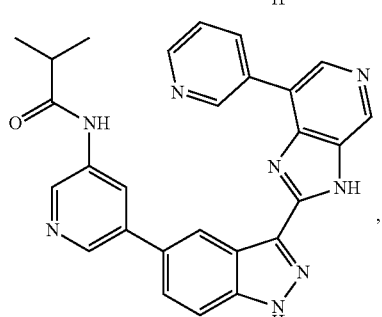,
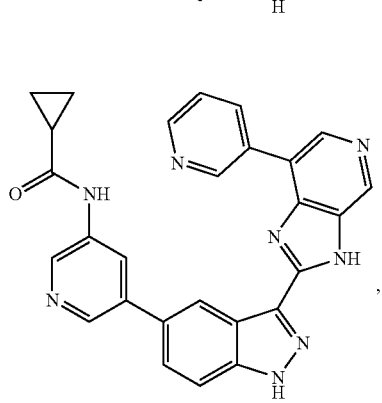,
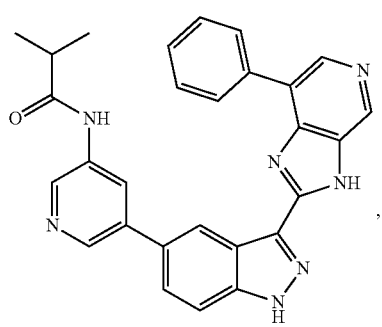,
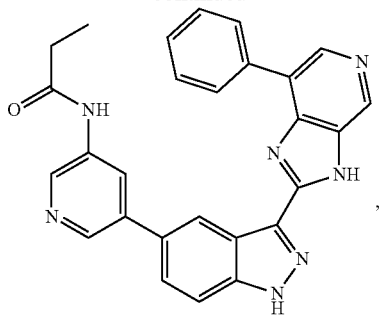,
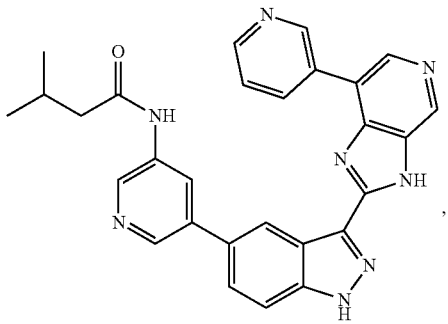,
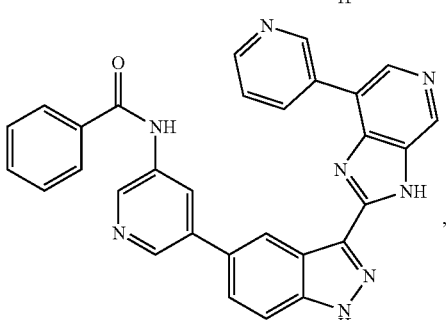,
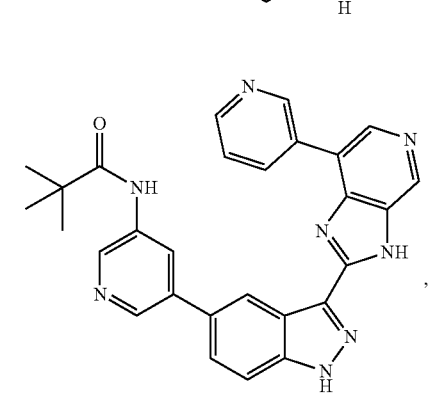,
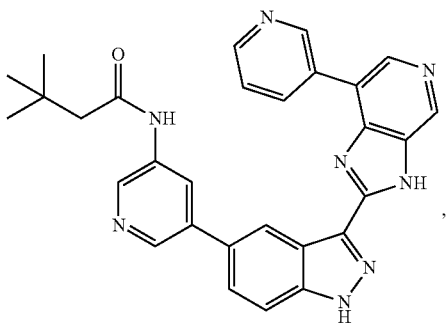, -continued
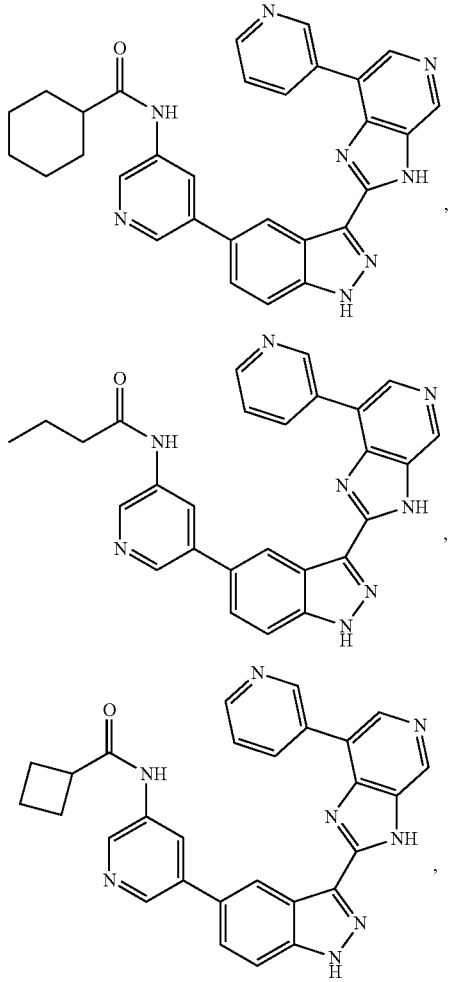
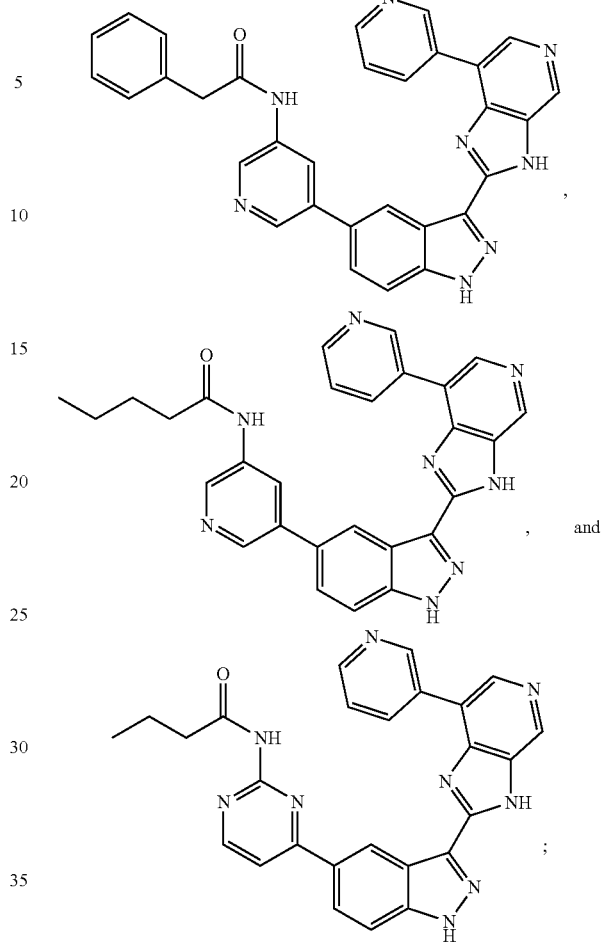
or a pharmaceutically acceptable salt thereof.
* * * * *